US006946562B2

(12) United States Patent
Diehl et al.

(10) Patent No.: US 6,946,562 B2
(45) Date of Patent: Sep. 20, 2005

(54) SYNTHESIS OF PEPTOID SUBSTITUTED AZOLE COMPOUNDS

(75) Inventors: Donald R. Diehl, Rochester, NY (US); Robert J. Niger, Rochester, NY (US); Hans F. Schmitthenner, Rush, NY (US); William J. Sonnefeld, Victor, NY (US); Richard P. Dunlap, Penfield, NY (US)

(73) Assignee: Eastman Kodak Company, Rochester, NY (US)

( * ) Notice: Subject to any disclaimer, the term of this patent is extended or adjusted under 35 U.S.C. 154(b) by 486 days.

(21) Appl. No.: 10/021,408

(22) Filed: Dec. 12, 2001

(65) Prior Publication Data

US 2003/0187188 A1 Oct. 2, 2003

(51) Int. Cl.[7] .............................................. C07D 249/00
(52) U.S. Cl. ................................ 548/262.4; 548/264.8; 548/266.4; 548/267.2; 530/333
(58) Field of Search ........................... 548/262.4, 264.8, 548/266.4, 267.2; 530/333

(56) References Cited

U.S. PATENT DOCUMENTS

| 3,810,761 A | 5/1974 | Bailey et al. |
| 5,256,526 A | 10/1993 | Suzuki et al. |
| 5,451,501 A | 9/1995 | Mizukawa et al. |
| 5,605,788 A | 2/1997 | Kawagishi et al. |
| 5,925,503 A | 7/1999 | Harder et al. |
| 5,972,587 A | 10/1999 | Romanet et al. |

OTHER PUBLICATIONS

Ronald N. Zuckermann, Janice M. Kerr, Stephen B. H. Kent and Walter H. Moos, "Efficient Method for the Preparation of Peptoids Oligo(N–substituted blycines) by Submonomer Solid–Phase Synthesis", J. Am. Chem. Soc. 1992, 114, pp. 10646–10647.

Klaus Kirschke, Erich Wolff, Matthias Ramm, Gerhard Lutze and Burkhard Schulz, "Selective Acylations of 3(5)–Alkyl–5(3)–amino–1H–pyrazoles and a new Pyrazolo5,1–c–1,2,4–triazole–Synthesis", Liebigs Ann. Chem. 1994, 10, pp. 1037–1042.

Ronald N. Zuckermann, Eric J. Martin, David C. Spellmeyer, Gregory B. Stauber, Kevin R. Shoemaker, Janice M. Kerr, Gianine M. Figliozzi, Dane A. Goff, Michael A. Siani, Reyna J. Simon, Steven C. Banville, Edward G. Brown, Liang Wang, Lutz S. Richter, and Walter H. Moos, "Discovery of Nanomolar Ligands for 7–Transmembrane G–Protein–Coupled Receptors from a Diverse N–(Substituted)glycine Peptoid Library", J. Med. Chem. 1994, 37, pp. 2678–2685.

Susan M. Miller, Reyna J. Simon, Simon Ng, Ronald N. Zuckerman, Janice M. Kerr, Walter H. Moos, "Proteolytic Studies of Homologous Peptide and N–Substituted Glycine Peptoid Oligomers", Biorganic & Medicinal Chemistry Letters, 1994, pp. 2657–2662.

Anthony W. Czarnik and Sheila H. DeWitt, "A Practical Guide to Combinatorial Chemistry", ACS Professional Reference Books, 1997, pp., 35, 57, 266–272, and 349–351.

Barry A. Bunin, "The Combinatorial Index", Academic Press, New York, 1998, pp. 112–113.

Eric M. Gordon and James F. Kerwin, Jr., "Combinatorial Chemistry and Molecular Diversity in Drug Discovery", John Wiley & Sons, New York, 1998, pp. 151–163.

Donald R. Diehl, Robert J. Niger, Hans F. Schmitthenner, William J. Sonnefeld and Richard P. Dunlap, "Imaging Materials Containing Peptoid Substituted Azole Couplers", U.S. Appl. No. 09/(D–83554) filed Dec. 12, 2001.

*Primary Examiner*—Kamal A. Saeed
*Assistant Examiner*—Robert Shiao
(74) *Attorney, Agent, or Firm*—Arthur E. Kluegel

(57) ABSTRACT

Disclosed is a process for the preparation of a peptoid substituted azole compound comprising reacting an amino functionalized azole compound with a resin bound peptoid oligomer bearing a terminal halogen substituent followed by cleavage of the resultant product from the resin surface using a fluorinated organic acid in an inert solvent.

13 Claims, No Drawings

SYNTHESIS OF PEPTOID SUBSTITUTED AZOLE COMPOUNDS

CROSS-REFERENCE TO RELATED APPLICATIONS

This application is related U.S. Ser. No. 10/021,408 filed on Dec. 12, 2001 and directed to a photographic element, coupler and dye.

FIELD OF THE INVENTION

This invention relates to the synthesis of peptoid ballasted dye-forming azole couplers using a solid phase organic chemistry method of synthesis including reacting an amino functionalized azole compound with a resin bound peptoid oligomer bearing a terminal halogen substituent followed by cleavage of the resultant product from the resin surface using a fluorinated organic acid in an inert solvent.

BACKGROUND OF THE INVENTION

In the photographic art color images are formed by the exposure of a silver halide light sensitive element containing organic dye forming couplers followed by processing in aqueous developer solutions containing an aromatic primary amine color developing agent. The resultant dyes formed are yellow, magenta, or cyan and result in the formation of a color image in the photographic element.

In the ink jet art images are formed by the deposition of a preformed colored ink or pigment upon a receiver material by use of a cartridge head loaded with a solution or dispersion of preformed dyes or pigments. The resultant images are colored as a result of the deposition of a varied mixture of the preformed inks or pigments.

Both of these imaging methods require novel color forming materials to improve the properties of the resultant images. Color forming image dyes must have desirable hues and good stability with little or no fading or discoloration under storage in the dark or when exposed to light. The couplers which form these dyes should have good coupling efficiency and lead to dye images with high contrast and high density in areas of maximum exposure and low density in areas of minimum exposure.

Couplers which have been recently received considerable interest in the imaging art include the pyrazolo[5,1-c]-1,2,4-triazole and the pyrazolo[1,5-b]-1,2,4-triazole heterocycles as shown below.

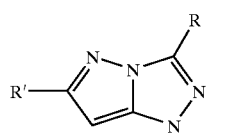

Pyrazolo[5, 1-c]-1, 2, 4-triazole

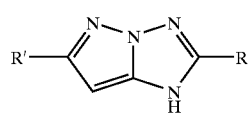

Pyrazolo[1, 5-b]-1, 2, 4-triazole

Other couplers include the imidazole, benzimidazole, and pyrroloazole couplers such as:

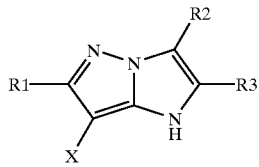

Imidazo[1,2-b]pyrazole

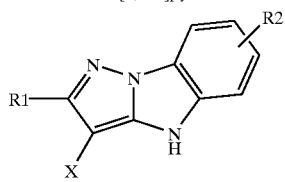

Pyrazolo[1,5-a]benzimidazole

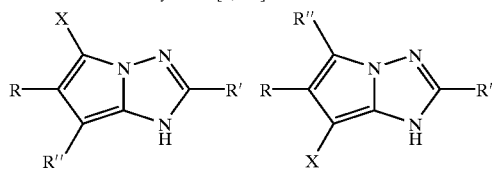

Pyrrolo[1, 2-b][1, 2, 4]triazoles

Other examples are the pyrazolone couplers as discussed hereinafter.

The R groups are substituents and X is H or a coupling-off group. It is well recognized by those skilled in the art that modifications of the structure of the substituents on the pyrazolotriazole heterocycle can have important effects on the dyes formed from these couplers, including improvements in dye image stability, etc. Thus, the researcher skilled in the art of photographic couplers is always seeking new substituents on the pyrazolotriazole heterocycle with an aim to discover ever better image dye properties. In recent years many patents have been issued on variations of the 3-alkyl substituted pyrazolo[5,1-c]-1,2,4-triazole couplers. These couplers have the required hue, contrast, and efficiency properties necessary to produce superior image dyes in modern photographic materials. Nevertheless, new substituent research continues.

In Bailey's original patent, U.S. Pat. No. 3,810,761 (May 1974), a wide range of substituents are described as useful in varying the hue and properties of pyrazolo[5,1-c]-1,2,4-triazole image dyes. In Harder's patent, U.S. Pat. No. 5,925,503 (July 1999), a tetramethylethyl link in the 3-position of the pyrazolo[5,1-c]-1,2,4-triazole is reported to provide image dyes with superior light stability and hue. In Harder's patented structure, see Coupler Structure A below, W is reported to represent $C(O)R^5$, $SO_2R^5$, or $P(O)(OR^6)_2$.

The properties of a pyrazolo[5,1-c]-1,2,4-triazole coupler similar to Structure A in which W is reported to be a CHR structural unit would be of interest to the skilled photographic coupler researcher. However, a synthesis method for such a pyrazolo[5,1-c]-1,2,4-triazole coupler is unknown. This is because the alkylation of the pendant amino functional group in Structure A by typical alkylating agents such as methyliodide, ethyliodide, methyltosylate, etc., results in the simultaneous alkylation of the ring nitrogen centers at position 1 and position 5 of the pyrazolo[5,1-c]-1,2,4-triazole ring thus producing products which contain multiple alkylated centers. Thus, the synthesis of new and improved pyrazolo[5,1-c]-1,2,4-triazoles has been limited in the past to those materials of the type described in Harder U.S. Pat. No. 5,925,503 (July 1999).

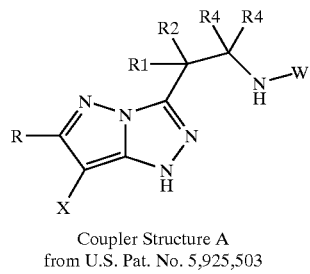

Coupler Structure A
from U.S. Pat. No. 5,925,503

Recently, Zuckermann, et. al., have described the solid phase organic chemistry synthesis of N-(substituted) glycines, a.k.a. "peptoids", from available and inexpensive starting materials. As used herein, a "peptoid" group means a substituent having a primary amine group linked to the remainder of the coupler compound, "Coup", with or without a linking group, through a chain of acetamide-groups as in the following:

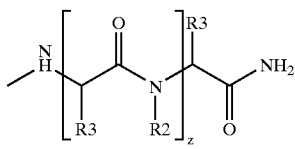

The technique of solid phase synthesis is known to those in the organic chemistry synthesis art and has been described in recent journal articles and books. The solid phase synthesis of the peptoid materials described by Zuckermann is assembled by repetition of a two step sequence from two readily available starting materials. The first step is acylation of Rink (more specifically described in the "Synthesis" section hereof) resin with bromoacetic acid. The second step is the addition of a primary amine resulting in a nucleophilic displacement of the bromine. Repetition of these two steps is reported to assemble an oligomeric peptoid. The choice of amines to be used in the assembly of the peptoid ballasts will be made by those skilled in the art based upon desired characteristics of size, shape, flexibility, degree of branching, molecular weight, and hydrophobicity among other attributes.

It has now been found that the use of the alkylation protocol as reported above does not result in the multiple alkylation of the ring nitrogen centers at position 1 and position 5 of the pyrazoloazole ring as demonstrated by such typical alkylating agents as methyliodide, ethyliodide, and methyltosylate, etc., but instead, results in the alkylation of the pendant amino functional group shown in Coupler Structure A without further alkylation occuring. This straight-forward synthesis enables the production for the first time of pyrazoloazole couplers bearing peptoid substituents in the W position of Coupler Structure A and enables the production of photographic elements and dyes using the couplers.

It would be useful to have photographic materials containing novel coupler compounds that produce dyes that exhibit desirable spectral absorption characteristics and good stability.

SUMMARY OF THE INVENTION

The invention provides a process for the preparation of a peptoid substituted azole compound comprising reacting an amino functionalized azole compound with a resin bound peptoid oligomer bearing a terminal halogen substituent followed by cleavage of the resultant product from the resin surface using a fluorinated organic acid in an inert solvent

DETAILED DESCRIPTION OF THE INVENTION

A detailed description of the invention is provided as follows. A peptoid group is a functionality depicted below as defined by R. N. Zuckermann, et. al., *J. Am. Chem. Soc.,* 1992, 10646–10647 in which R is generally defined as a side chain and X as an $NH_2$, and n is a number equal to or greater than zero,

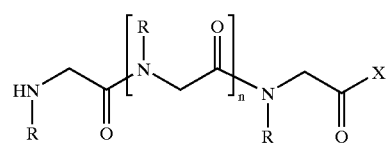

or, for purposes of this invention,

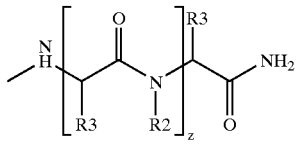

The couplers useful in the element of the invention contain a peptoid group represented by the above formula. The couplers form dyes having desirable hue and stability for imaging. They conveniently contain up to 7, suitably 2–4 acetamide groups, and they are desirably linked to the coupler nucleus by a tetramethyl ethyl group.

Azole couplers are well-known and include one ring as in the pyrazolones or two fused 5-membered rings at least one being an azole. Azole couplers include, for example, the pyrazolo[5,1-c]-1,2,4-triazole, pyrazolo[1,5-b]-1,2,4-triazole, imidazo[1,2-b]pyrazole, pyrazolo[1,5-a] benzimidazole and pyrrolo [1,2-b][1,2,4]triazole heterocycles as shown below in which each R group is a substituent and X is H or a coupling off group.

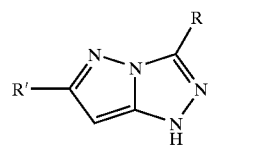

Pyrazolo [5, 1-c]-1, 2, 4-triazole

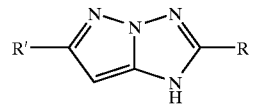

Pyrazolo [1, 5-b]-1, 2, 4-triazole

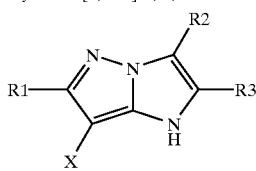

Imidazo[1,2-b]pyrazole

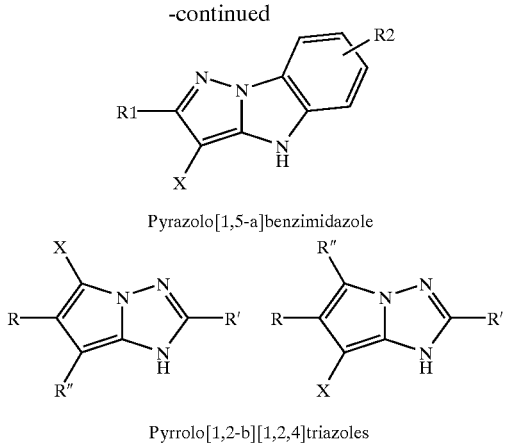

Pyrazolo[1,5-a]benzimidazole

Pyrrolo[1,2-b][1,2,4]triazoles

The R groups are substituents and X is H or a coupling-off group. More commonly, the second ring is a triazole such as the 1H-pyrazolo[5,1-c]-1,2,4-triazole and a 1H-pyrazolo[1,5-b]-1,2,4-triazole, as shown above.

A generic formula that represents a suitably substituted bicyclic azole coupler is shown in Formula I below:

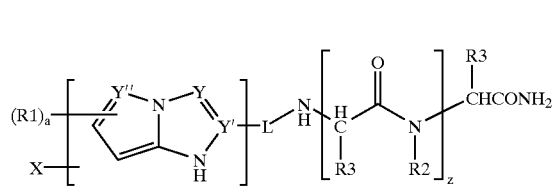

wherein
each R1 represents an independently selected substituent group and a is 0–4;
each R2 represents an independently selected substituent group;
each R3 represents hydrogen or an independently selected substituent group;
L represents a single bond or a chain of atoms containing one or more of carbon, nitrogen, oxygen, and sulfur atoms;
each Y, Y', and Y" independently represents a carbon or nitrogen atom with the proviso that at least one of Y, Y' or Y" is a carbon, and that Y and Y' may represent the carbons necessary to form part of a fused six membered aromatic ring, and provided further that, if Y and Y' represents the carbons necessary to form part of a fused six membered aromatic ring, the L linking group is not attached directly to the Y or Y' atom, and Y, Y' and Y" may be further substituted by R1 when not directly attached to L;
X is a hydrogen atom, a halogen atom, a carboxy group, an acyl group, or a group bonded to the coupling position through an oxygen, nitrogen, or sulfur atom, and
Z is 1–6.

Desirably a is at least 1 and each R1 represents a substituent such as those listed hereinafter. Typical examples of such groups include methyl, ethyl, butyl, dodecyl, octadecyl, icosenyl, iso-propyl, tert-butyl, tert-octyl, tert-dodecyl, cyclohexyl, cyclopentyl, allyl, vinyl, 2-hexadecenyl, and propargyl groups. Especially preferred R1 substituents are alkyl, aryl, alkoxy, amino, anilino, alkoxycarbonyl, carbamoyl, acyl, cyano, sulfone, and sulfonamido groups and particularly t-butyl, phenyl, ethylcarboxyl, methylcyclopropyl, and adamantyl groups.

R2 may be a substituent such as an alkyl, cycloalkl, aryl, or heteroaryl group. Useful examples include groups containing up to 20 carbon atoms such as cyclohexyl, 2-ethylhexyl, dodecyl, 3-ethoxypropyl, cyclohexylmethyl, benzyl, phenyl, and 1-(3-propyl)-2-pyrrolidinone groups.

R3 may be hydrogen or a substituent group such as one of the substituent groups specified for R1. Hydrogen is conveniently employed The group X is useful as hydrogen or a leaving (or coupling-off) group. Examples of groups represented by X include but are not limited to hydrogen or any of the coupling off groups known in the art as described more fully hereinafter. Especially preferred X groups include hydrogen and halogen.

The atoms represented by Y, Y', and Y" are nitrogen or carbon. At least one of them is carbon and Y and Y' may join to form a fused six-membered aromatic ring so long as the group L is not bonded to Y or Y'.

The value of "Z" is indicative of the length of the peptoid chain. Typically Z is 1–3.

Azomethine dyes of the invention are formed upon reaction of an oxidized primary aromatic amine with the azole couplers useful in this invention. Preferred dyes of this invention upon suitable dispersion preparation and ink jet coating on a suitable receiver provide magenta images with a spectral absorption peak in the region of the spectrum from 500 to 600 nm with a half band width of less then 120 nm, preferably less than 100 nm and most preferably less than 90 nm and exhibit the property of good light and dark stability. The couplers of this invention may also optionally be prepared into suitable dispersions which when coated upon a support bearing a light sensitive silver halide emulsion and further after exposure and processing in an oxidized primary aromatic amine developing solution may produce magenta images with a spectral absorption peak in the region of the spectrum from 500 to 600 nm with a half band width of less then 120 nm, preferably less than 100 nm and most preferably less than 90 nm and exhibit the property of good light and dark stability.

The following are examples of couplers useful in the invention:

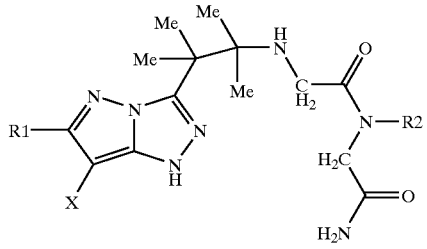

A

| Invention Coupler | R₁ | R₂ | X |
|---|---|---|---|
| A1 | t-Bu | cyclohexyl | H |
| A2 | t-Bu | 2-ethylhexyl | H |
| A3 | t-Bu | dodecyl | H |
| A4 | t-Bu | 3-ethoxypropyl | H |
| A5 | t-Bu | cyclohexanemethyl | H |
| A6 | t-Bu | benzyl | H |
| A7 | t-Bu | phenyl | H |
| A8 | t-Bu | 1-(3-propyl)-2-pyrrolidinone | H |
| A9 | t-Bu | cyclohexyl | Cl |
| A10 | t-Bu | 2-ethylhexyl | Cl |

-continued

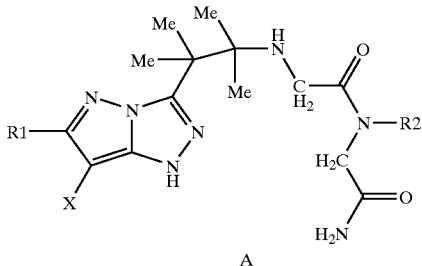

A

| Invention Coupler | R₁ | R₂ | X |
|---|---|---|---|
| A11 | t-Bu | dodecyl | Cl |
| A12 | t-Bu | 3-ethoxypropyl | Cl |
| A13 | t-Bu | cyclohexanemethyl | Cl |
| A14 | t-Bu | benzyl | Cl |
| A15 | Ph | cyclohexyl | H |
| A16 | Ph | 2-ethylhexyl | H |
| A17 | Ph | dodecyl | H |
| A18 | Ph | 3-ethoxypropyl | H |
| A19 | Ph | cyclohexanemethyl | H |
| A20 | Ph | benzyl | H |
| A21 | CO2Et | cyclohexyl | H |
| A22 | CO2Et | 2-ethylhexyl | H |
| A23 | CO2Et | dodecyl | H |
| A24 | CO2Et | 3-ethoxypropyl | H |
| A25 | CO2Et | cyclohexanemethyl | H |
| A26 | CO2Et | benzyl | H |

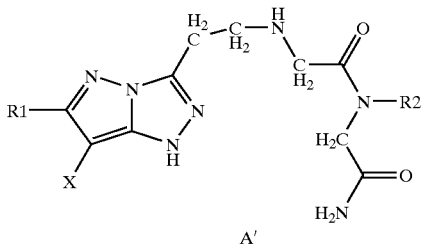

A'

| Invention Coupler | R₁ | R₂ | X |
|---|---|---|---|
| A'1 | t-Bu | cyclohexyl | H |
| A'2 | t-Bu | 2-ethylhexyl | H |
| A'3 | t-Bu | dodecyl | H |
| A'4 | t-Bu | 3-ethoxypropyl | H |
| A'5 | t-Bu | cyclohexanemethyl | H |
| A'6 | t-Bu | benzyl | H |
| A'7 | t-Bu | phenyl | H |
| A'8 | t-Bu | 1-(3-propyl)-2-pyrrolidinone | H |
| A'9 | t-Bu | cyclohexyl | Cl |
| A'10 | t-Bu | 2-ethylhexyl | Cl |
| A'11 | t-Bu | dodecyl | Cl |
| A'12 | t-Bu | 3-ethoxypropyl | Cl |
| A'13 | t-Bu | cyclohexanemethyl | Cl |
| A'14 | t-Bu | benzyl | Cl |
| A'15 | Me | cyclohexyl | H |
| A'16 | Me | 2-ethylhexyl | H |
| A'17 | Me | dodecyl | H |
| A'18 | Me | 3-ethoxypropyl | H |
| A'19 | Me | cyclohexanemethyl | H |
| A'20 | Me | benzyl | H |

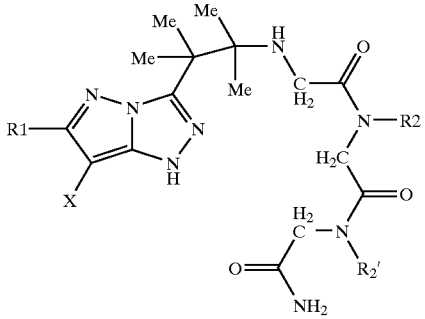

B

| Invention Coupler | R₁ | R₂ | R₂' | X |
|---|---|---|---|---|
| B1 | t-Bu | cyclohexyl | cyclohexyl | H |
| B2 | t-Bu | 2-ethylhexyl | cyclohexyl | H |
| B3 | t-Bu | dodecyl | cyclohexyl | H |
| B4 | t-Bu | cyclohexyl | 2-ethylhexyl | H |
| B5 | t-Bu | 2-ethylhexyl | 2-ethylhexyl | H |
| B6 | t-Bu | dodecyl | 2-ethylhexyl | H |
| B7 | t-Bu | cyclohexyl | dodecyl | H |
| B8 | t-Bu | 2-ethylhexyl | dodecyl | H |
| B9 | t-Bu | dodecyl | dodecyl | H |
| B10 | t-Bu | hexyl | hexyl | H |
| B11 | t-Bu | 3-ethoxypropyl | hexyl | H |
| B12 | t-Bu | cyclohexanemethyl | hexyl | H |
| B13 | t-Bu | benzyl | hexyl | H |
| B14 | t-Bu | hexyl | 3-ethoxypropyl | H |
| B15 | t-Bu | 3-ethoxypropyl | 3-ethoxypropyl | H |
| B16 | t-Bu | cyclohexanemethyl | 3-ethoxypropyl | H |
| B17 | t-Bu | benzyl | 3-ethoxypropyl | H |
| B18 | t-Bu | hexyl | cyclohexanemethyl | H |
| B19 | t-Bu | 3-ethoxypropyl | cyclohexanemethyl | H |
| B20 | t-Bu | cyclohexanemethyl | cyclohexanemethyl | H |
| B21 | t-Bu | benzyl | cyclohexanemethyl | H |
| B22 | t-Bu | hexyl | benzyl | H |
| B23 | t-Bu | 3-ethoxypropyl | benzyl | H |
| B24 | t-Bu | cyclohexanemethyl | benzyl | H |
| B25 | t-Bu | benzyl | benzyl | H |
| B26 | t-Bu | cyclohexyl | cyclohexyl | Cl |
| B27 | t-Bu | 2-ethylhexyl | cyclohexyl | Cl |
| B28 | t-Bu | dodecyl | cyclohexyl | Cl |
| B29 | Ph | cyclohexyl | cyclohexyl | H |
| B30 | Ph | 2-ethylhexyl | cyclohexyl | H |
| B31 | Ph | dodecyl | cyclohexyl | H |
| B32 | CO2Et | cyclohexyl | cyclohexyl | H |
| B33 | CO2Et | 2-ethylhexyl | cyclohexyl | H |
| B34 | CO2Et | dodecyl | cyclohexyl | H |

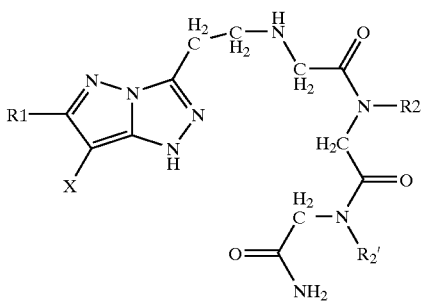

B'

| Invention Coupler | R₁ | R₂ | R₂' | X |
|---|---|---|---|---|
| B'1 | t-Bu | cyclohexyl | cyclohexyl | H |
| B'2 | t-Bu | 2-ethylhexyl | cyclohexyl | H |

-continued

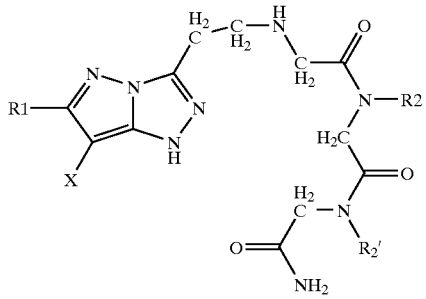

B'

| Invention Coupler | R₁ | R₂ | R₂' | X |
|---|---|---|---|---|
| B'3 | t-Bu | dodecyl | cyclohexyl | H |
| B'4 | t-Bu | cyclohexyl | 2-ethylhexyl | H |
| B'5 | t-Bu | 2-ethylhexyl | 2-ethylhexyl | H |
| B'6 | t-Bu | dodecyl | 2-ethylhexyl | H |
| B'7 | t-Bu | cyclohexyl | dodecyl | H |
| B'8 | t-Bu | 2-ethylhexyl | dodecyl | H |
| B'9 | t-Bu | dodecyl | dodecyl | H |
| B'10 | t-Bu | hexyl | hexyl | H |
| B'11 | t-Bu | 3-ethoxypropyl | hexyl | H |
| B'12 | t-Bu | cyclohexanemethyl | hexyl | H |
| B'13 | t-Bu | benzyl | hexyl | H |
| B'14 | t-Bu | hexyl | 3-ethoxypropyl | H |
| B'15 | t-Bu | 3-ethoxypropyl | 3-ethoxypropyl | H |
| B'16 | t-Bu | cyclohexanemethyl | 3-ethoxypropyl | H |
| B'17 | t-Bu | benzyl | 3-ethoxypropyl | H |

-continued

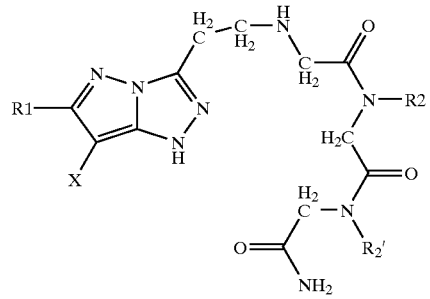

B'

| Invention Coupler | R₁ | R₂ | R₂' | X |
|---|---|---|---|---|
| B'18 | t-Bu | hexyl | cyclohexanemethyl | H |
| B'19 | t-Bu | 3-ethoxypropyl | cyclohexanemethyl | H |
| B'20 | t-Bu | cyclohexanemethyl | cyclohexanemethyl | H |
| B'21 | t-Bu | benzyl | cyclohexanemethyl | H |
| B'22 | t-Bu | hexyl | benzyl | H |
| B'23 | t-Bu | 3-ethoxypropyl | benzyl | H |
| B'24 | t-Bu | cyclohexanemethyl | benzyl | H |
| B'25 | t-Bu | benzyl | benzyl | H |
| B'26 | t-Bu | cyclohexyl | cyclohexyl | Cl |
| B'27 | t-Bu | 2-ethylhexyl | cyclohexyl | Cl |
| B'28 | t-Bu | dodecyl | cyclohexyl | Cl |
| B'29 | Me | cyclohexyl | cyclohexyl | H |
| B'30 | Me | 2-ethylhexyl | cyclohexyl | H |
| B'31 | Me | dodecyl | cyclohexyl | H |

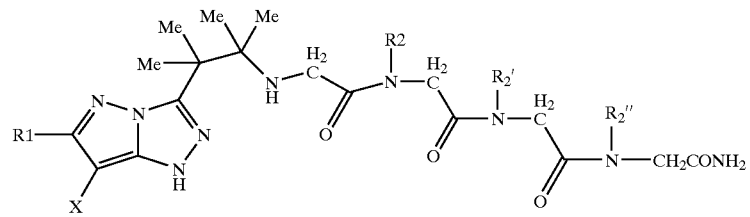

C

| Invention Coupler | R₁ | R₂ | R₂' | R₂" | X |
|---|---|---|---|---|---|
| C1 | t-Bu | cyclohexyl | cyclohexyl | cyclohexyl | H |
| C2 | t-Bu | 2-ethylhexyl | cyclohexyl | 2-ethylhexyl | H |
| C3 | t-Bu | dodecyl | cyclohexyl | dodecyl | H |
| C4 | t-Bu | cyclohexyl | 2-ethylhexyl | cyclohexyl | H |
| C5 | t-Bu | 2-ethylhexyl | 2-ethylhexyl | 2-ethylhexyl | H |
| C6 | t-Bu | dodecyl | 2-ethylhexyl | dodecyl | H |
| C7 | t-Bu | cyclohexyl | dodecyl | cyclohexyl | H |
| C8 | t-Bu | 2-ethylhexyl | dodecyl | 2-ethylhexyl | H |
| C9 | t-Bu | dodecyl | dodecyl | dodecyl | H |
| C10 | t-Bu | hexyl | hexyl | hexyl | H |
| C11 | t-Bu | 3-ethoxypropyl | hexyl | 3-ethoxypropyl | H |
| C12 | t-Bu | cyclohexanemethyl | hexyl | cyclohexanemethyl | H |
| C13 | t-Bu | benzyl | hexyl | benzyl | H |
| C14 | t-Bu | hexyl | 3-ethoxypropyl | hexyl | H |
| C15 | t-Bu | 3-ethoxypropyl | 3-ethoxypropyl | 3-ethoxypropyl | H |
| C16 | t-Bu | cyclohexanemethyl | 3-ethoxypropyl | cyclohexanemethyl | H |
| C17 | t-Bu | benzyl | 3-ethoxypropyl | benzyl | H |
| C18 | t-Bu | hexyl | cyclohexanemethyl | hexyl | H |
| C19 | t-Bu | 3-ethoxypropyl | cyclohexanemethyl | 3-ethoxypropyl | H |

-continued

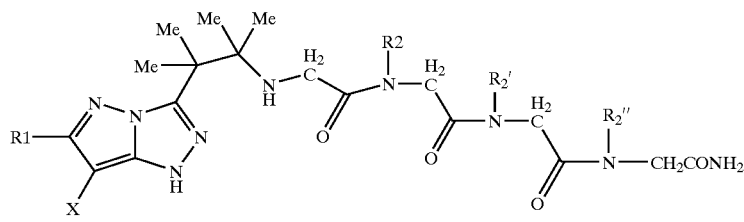

C

| Invention Coupler | R₁ | R₂ | R₂' | R₂" | X |
|---|---|---|---|---|---|
| C20 | t-Bu | cyclohexanemethyl | cyclohexanemethyl | cyclohexanemethyl | H |
| C21 | t-Bu | benzyl | cyclohexanemethyl | benzyl | H |
| C22 | t-Bu | hexyl | benzyl | hexyl | H |
| C23 | t-Bu | 3-ethoxypropyl | benzyl | 3-ethoxypropyl | H |
| C24 | t-Bu | cyclohexanemethyl | benzyl | cyclohexanemethyl | H |
| C25 | t-Bu | benzyl | benzyl | benzyl | H |
| C26 | t-Bu | cyclohexyl | cyclohexyl | cyclohexyl | Cl |
| C27 | t-Bu | 2-ethylhexyl | cyclohexyl | 2-ethylhexyl | Cl |
| C28 | t-Bu | dodecyl | cyclohexyl | dodecyl | Cl |
| C29 | Ph | cydohexyl | cyclohexyl | cyclohexyl | H |
| C30 | Ph | 2-ethylhexyl | cyclohexyl | 2-ethylhexyl | H |
| C31 | Ph | dodecyl | cyclohexyl | dodecyl | H |
| C32 | CO2Et | cyclohexyl | cyclohexyl | cyclohexyl | H |
| C33 | CO2Et | 2-ethylhexyl | cyclohexyl | 2-ethylhexyl | H |
| C34 | CO2Et | dodecyl | cyclohexyl | dodecyl | H |

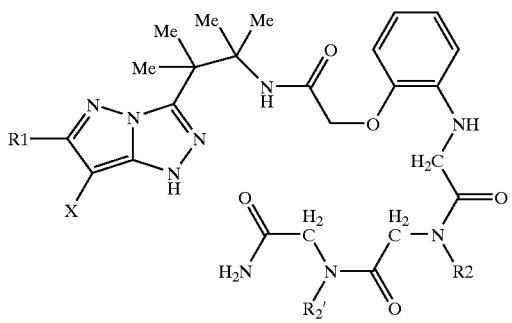

D

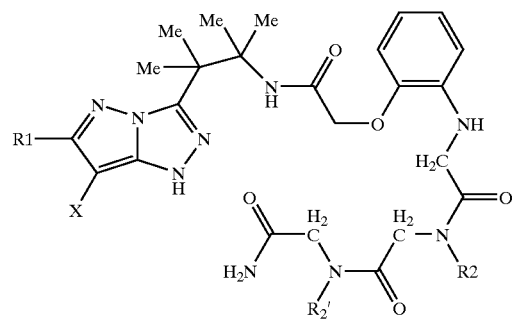

D

| Invention Coupler | R₁ | R₂ | R₂' | X |
|---|---|---|---|---|
| D1 | t-Bu | hexyl | hexyl | H |
| D2 | t-Bu | 3-ethoxypropyl | hexyl | H |
| D3 | t-Bu | cyclohexanemethyl | hexyl | H |
| D4 | t-Bu | benzyl | hexyl | H |
| D5 | t-Bu | hexyl | 3-ethoxypropyl | H |
| D6 | t-Bu | 3-ethoxypropyl | 3-ethoxypropyl | H |
| D7 | t-Bu | cyclohexanemethyl | 3-ethoxypropyl | H |
| D8 | t-Bu | benzyl | 3-ethoxypropyl | H |
| D9 | t-Bu | hexyl | cyclohexanemethyl | H |
| D10 | t-Bu | 3-ethoxypropyl | cyclohexanemethyl | H |
| D11 | t-Bu | cyclohexanemethyl | cyclohexanemethyl | H |
| D12 | t-Bu | benzyl | cyclohexanemethyl | H |
| D13 | t-Bu | hexyl | benzyl | H |
| D14 | t-Bu | 3-ethoxypropyl | benzyl | H |
| D15 | t-Bu | cyclohexanemethyl | benzyl | H |
| D16 | t-Bu | benzyl | benzyl | H |
| D17 | t-Bu | cyclohexyl | cyclohexyl | H |
| D18 | t-Bu | 2-ethylhexyl | cyclohexyl | H |
| D19 | t-Bu | dodecyl | cyclohexyl | H |
| D20 | t-Bu | cyclohexyl | 2-ethylhexyl | H |
| D21 | t-Bu | 2-ethylhexyl | 2-ethylhexyl | H |
| D22 | t-Bu | dodecyl | 2-ethylhexyl | H |
| D23 | t-Bu | cyclohexyl | dodecyl | Cl |
| D24 | t-Bu | 2-ethylhexyl | dodecyl | Cl |
| D25 | t-Bu | dodecyl | dodecyl | Cl |
| D26 | t-Bu | dodecyl | hexyl | Cl |
| D27 | t-Bu | dodecyl | 3-ethoxypropyl | H |
| D28 | t-Bu | dodecyl | cyclohexanemethyl | H |
| D29 | t-Bu | 2-ethylhexyl | hexyl | H |
| D30 | t-Bu | 2-ethylhexyl | 3-ethoxypropyl | H |
| D31 | t-Bu | 2-ethylhexyl | cyclohexanemethyl | H |
| D32 | t-Bu | cyclohexyl | hexyl | H |
| D33 | t-Bu | cyclohexyl | 3-ethoxypropyl | H |
| D34 | t-Bu | cyclohexyl | cyclohexanemethyl | H |

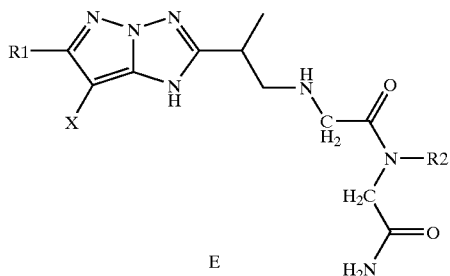

E

| Invention Coupler | R₁ | R₂ | X |
|---|---|---|---|
| E1 | t-Bu | cyclohexyl | H |
| E2 | t-Bu | 2-ethylhexyl | H |
| E3 | t-Bu | dodecyl | H |
| E4 | t-Bu | 3-ethoxypropyl | H |
| E5 | t-Bu | cyclohexanemethyl | H |
| E6 | t-Bu | benzyl | H |
| E7 | t-Bu | phenyl | H |
| E8 | t-Bu | 1-(3-propyl)-2-pyrrolidinone | H |
| E9 | t-Bu | cyclohexyl | Cl |
| E10 | t-Bu | 2-ethylhexyl | Cl |
| E11 | t-Bu | dodecyl | Cl |
| E12 | t-Bu | 3-ethoxypropyl | Cl |
| E13 | t-Bu | cyclohexanemethyl | Cl |
| E14 | t-Bu | benzyl | Cl |

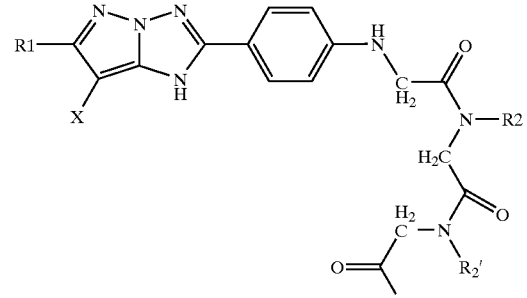

F

| Invention Coupler | R₁ | R₂ | R₂' | X |
|---|---|---|---|---|
| F23 | t-Bu | cyclohexyl | dodecyl | Cl |
| F24 | t-Bu | 2-ethylhexyl | dodecyl | Cl |
| F25 | t-Bu | dodecyl | dodecyl | Cl |
| F26 | t-Bu | dodecyl | hexyl | Cl |
| F27 | t-Bu | dodecyl | 3-ethoxypropyl | H |
| F28 | t-Bu | dodecyl | cyclohexanemethyl | H |
| F29 | t-Bu | 2-ethylhexyl | hexyl | H |
| F30 | t-Bu | 2-ethylhexyl | 3-ethoxypropyl | H |
| F31 | t-Bu | 2-ethylhexyl | cyclohexanemethyl | H |
| F32 | t-Bu | cyclohexyl | hexyl | H |
| F33 | t-Bu | cyclohexyl | 3-ethoxypropyl | H |
| F34 | t-Bu | cyclohexyl | cyclohexanemethyl | H |

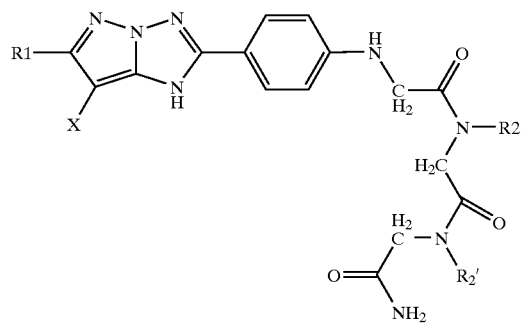

F

| Invention Coupler | R₁ | R₂ | R₂' | X |
|---|---|---|---|---|
| F1 | t-Bu | hexyl | hexyl | H |
| F2 | t-Bu | 3-ethoxypropyl | hexyl | H |
| F3 | t-Bu | cyclohexanemethyl | hexyl | H |
| F4 | t-Bu | benzyl | hexyl | H |
| F5 | t-Bu | hexyl | 3-ethoxypropyl | H |
| F6 | t-Bu | 3-ethoxypropyl | 3-ethoxypropyl | H |
| F7 | t-Bu | cyclohexanemethyl | 3-ethoxypropyl | H |
| F8 | t-Bu | benzyl | 3-ethoxypropyl | H |
| F9 | t-Bu | hexyl | cyclohexanemethyl | H |
| F10 | t-Bu | 3-ethoxypropyl | cyclohexanemethyl | H |
| F11 | t-Bu | cyclohexanemethyl | cyclohexanemethyl | H |
| F12 | t-Bu | benzyl | cyclohexanemethyl | H |
| F13 | t-Bu | hexyl | benzyl | H |
| F14 | t-Bu | 3-ethoxypropyl | benzyl | H |
| F15 | t-Bu | cyclohexanemethyl | benzyl | H |
| F16 | t-Bu | benzyl | benzyl | H |
| F17 | t-Bu | cyclohexyl | cyclohexyl | H |
| F18 | t-Bu | 2-ethylhexyl | cyclohexyl | H |
| F19 | t-Bu | dodecyl | cyclohexyl | H |
| F20 | t-Bu | cyclohexyl | 2-ethylhexyl | H |
| F21 | t-Bu | 2-ethylhexyl | 2-ethylhexyl | H |
| F22 | t-Bu | dodecyl | 2-ethylhexyl | H |

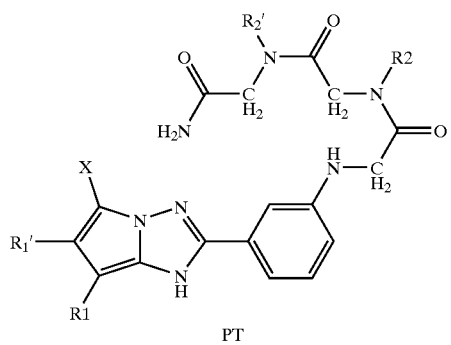

PT

| Invention Coupler | R₁ | R₁' | R₂ | R₂' | X |
|---|---|---|---|---|---|
| PT1 | CN | CO₂Et | hexyl | hexyl | H |
| PT2 | CN | CO₂Et | 3-ethoxypropyl | hexyl | H |
| PT3 | CN | CO₂Et | cyclohexanemethyl | hexyl | H |
| PT4 | CN | CO₂Et | benzyl | hexyl | H |
| PT5 | CN | CO₂Et | hexyl | 3-ethoxypropyl | H |
| PT6 | CN | CO₂Et | 3-ethoxypropyl | 3-ethoxypropyl | H |
| PT7 | CN | CO₂Et | cyclohexanemethyl | 3-ethoxypropyl | H |
| PT8 | CN | CO₂Et | benzyl | 3-ethoxypropyl | H |
| PT9 | CN | CN | hexyl | cyclohexanemethyl | H |
| PT10 | CN | CN | 3-ethoxypropyl | cyclohexanemethyl | H |
| PT11 | CN | CN | cyclohexanemethyl | cyclohexanemethyl | H |
| PT12 | CN | CN | benzyl | cyclohexanemethyl | H |
| PT13 | CN | CN | hexyl | benzyl | H |
| PT14 | CN | CN | 3-ethoxypropyl | benzyl | H |

-continued

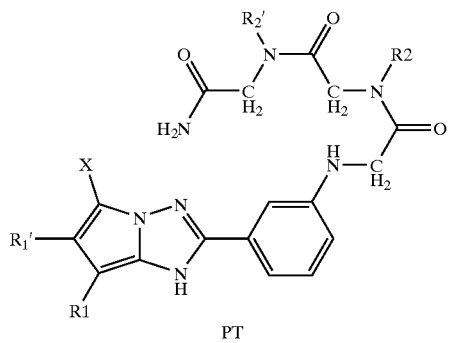

PT

| Invention Coupler | R₁ | R₁' | R₂ | R₂' | X |
|---|---|---|---|---|---|
| PT15 | CN | CN | cyclohex-anemethyl | benzyl | H |
| PT16 | CN | CN | benzyl | benzyl | H |
| PT17 | CONHPh | CN | 2-ethylhexyl | cyclohexanemethyl | H |
| PT18 | CONHPh | CN | dodecyl | cyclohexanemethyl | H |
| PT19 | CONHPh | CN | cyclohex-anemethyl | 2-ethylhexyl | H |
| PT20 | CONHPh | CN | 2-ethylhexyl | 2-ethylhexyl | H |

The couplers of the present invention may be used as intermediates to prepare novel dyes. As described by Bailey in EP 1,253,933 such novel dyes may be useful in sensitized silver halide photographic materials as filter dyes or sensitizing dyes. Such dyes may also be useful as textile dyes and in more modem imaging applications such as a thermal dye transfer imaging processes and as ink jet dyes. For example, azomethine dyes of the generic Dye Structure GI are shown below.

Generic Dye Structure GI

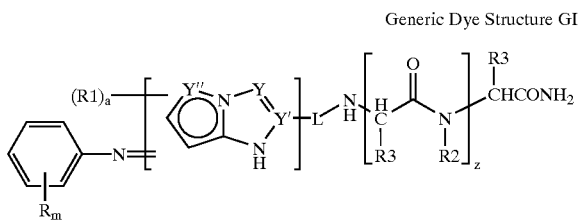

Most especially preferred dyes are the azomethine dyes of generic Dye Structure II below. These dyes are easily prepared by the reaction of oxidized primary aromatic amines with the novel pyrazolo[5,1-c]-1,2,4-triazole couplers of this invention. These new dyes have good extinction and high optical density with low unwanted absorbance at wavelengths of light which reduce the desirable hue of the dye. The azomethine dyes prepared from the couplers of this invention have been found to have good light stability. This particular stability may result from the intramolecular hydrogen bonding of the N1 heterocycle center of the pyrazolo[5,1-c]-1,2,4-triazole coupler with the terminal primary amide functionality of the peptoid substituent.

Generic Dye Structure II

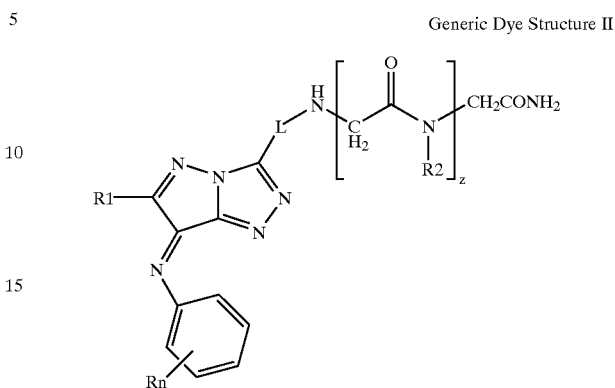

One skilled in the art of image coupler synthesis may recognize that L groups in coupler Structure I may represent alkyl, aryl, or heteroaryl groups which may in turn be further substituted. Examples of such substituents may typically include those described below but are not limited by those listed.

The variables in the dye structures are defined as shown above for formula I.

The novel dyes of Dye Structure II may be represented by the couplers bearing a peptoid functionality as part of the 3-substituent on the pyrazolo[5,1-c]-1,2,4-triazole heterocycle.

In the novel Dye Structure II the substituents Rn represent one or more substituents defining typical aminophenol and p-phenylenediamine derivatives which may include but are not limited by the following: o-aminophenol, p-aminophenol, 5-amino-2-hydroxytoluene, 2-amino-3-hydroxytoluene, 2-hydroxy-3-amino-1,4-dimethylbenzene, N,N-diethyl-p-phenylenediamine, 2-amino-5-diethylaminotoluene, 2-amino-5-(N-ethyl-N-laurylamino) toluene, 4-[N-ethyl-N-(beta-hydroxyethyl)amino]aniline, 2-methyl-4-[N-ethyl-N-(beta-hydroxyethyl)amino]aniline, 4-amino-3-methyl-N-ethyl-N-[beta-(methanesulfonamido) ethyl]aniline, N-(2-amino-5-diethylaminophenylethyl) methanesulfonamide, N,N-dimethyl-p-phenylenediamine monohydrochloride, 4-N,N-diethyl-2-methylphenylenediamine monohydrochloride, 4-(N-ethyl-N-2-methanesulfonylaminoethyl)-2-methylphenylenediamine sesquisulfate monohydrate, 4-(N-ethyl-N-2-hydroxyethyl)-2-methylphenylenediamine sulfate, 4-amino-3-methyl-N-ethyl-N-methoxyethylaniline, 4-amino-3-methyl-N-ethyl-N-beta-ethoxyethylaniline, 4-amino-3-methyl-N-ethyl-N-beta-butoxyethylaniline, and 4-N,N-diethyl-2,2'-methanesulfonylaminoethylphenylenediamine hydrochloride.

Particularly preferred are the p-phenylenediamines and especially the N,N-dialkyl-p-phenylenediamines in which the alkyl groups or the aromatic nucleus can be substituted or unsubstituted.

Hereunder, the typical examples of the azomethine dyes relating to the present invention will be given. However, the present invention shall not be limited thereto.

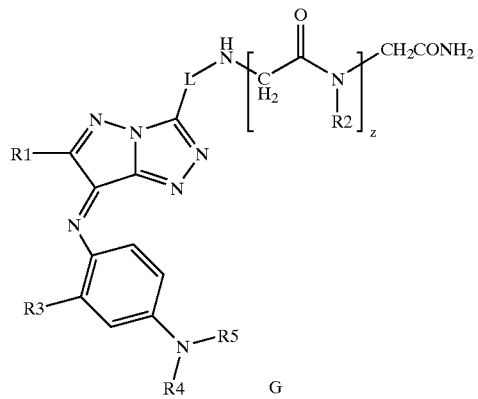

| Invention Dye | Invention Coupler | R3 | R4 | R5 |
|---|---|---|---|---|
| G1 | A1 | Me | Et | —CH$_2$CH$_2$NHSO$_2$Me |
| G2 | A2 | Me | Et | —CH$_2$CH$_2$NHSO$_2$Me |
| G3 | A3 | Me | Et | —CH$_2$CH$_2$NHSO$_2$Me |
| G4 | B1 | Me | Et | —CH$_2$CH$_2$NHSO$_2$Me |
| G5 | B2 | Me | Et | —CH$_2$CH$_2$NHSO$_2$Me |
| G6 | B3 | Me | Et | —CH$_2$CH$_2$NHSO$_2$Me |
| G7 | B4 | Me | Et | —CH$_2$CH$_2$NHSO$_2$Me |
| G8 | B5 | Me | Et | —CH$_2$CH$_2$NHSO$_2$Me |
| G9 | B6 | Me | Et | —CH$_2$CH$_2$NHSO$_2$Me |
| G10 | B7 | Me | Et | —CH$_2$CH$_2$NHSO$_2$Me |
| G11 | B8 | Me | Et | —CH$_2$CH$_2$NHSO$_2$Me |
| G12 | B9 | Me | Et | —CH$_2$CH$_2$NHSO$_2$Me |
| G13 | B10 | Me | Et | —CH$_2$CH$_2$NHSO$_2$Me |
| G14 | B11 | Me | Et | —CH$_2$CH$_2$NHSO$_2$Me |
| G15 | B12 | Me | Et | —CH$_2$CH$_2$NHSO$_2$Me |
| G16 | B13 | Me | Et | —CH$_2$CH$_2$NHSO$_2$Me |
| G17 | B14 | Me | Et | —CH$_2$CH$_2$NHSO$_2$Me |
| G18 | B15 | Me | Et | —CH$_2$CH$_2$NHSO$_2$Me |
| G19 | B16 | Me | Et | —CH$_2$CH$_2$NHSO$_2$Me |
| G20 | B17 | Me | Et | —CH$_2$CH$_2$NHSO$_2$Me |
| G21 | B18 | Me | Et | —CH$_2$CH$_2$NHSO$_2$Me |
| G22 | B19 | Me | Et | —CH$_2$CH$_2$NHSO$_2$Me |
| G23 | B20 | Me | Et | —CH$_2$CH$_2$NHSO$_2$Me |
| G24 | B21 | Me | Et | —CH$_2$CH$_2$NHSO$_2$Me |
| G25 | B22 | Me | Et | —CH$_2$CH$_2$NHSO$_2$Me |
| G26 | B23 | Me | Et | —CH$_2$CH$_2$NHSO$_2$Me |
| G27 | B24 | Me | Et | —CH$_2$CH$_2$NHSO$_2$Me |
| G28 | B25 | Me | Et | —CH$_2$CH$_2$NHSO$_2$Me |
| G29 | D1 | Me | Et | —CH$_2$CH$_2$NHSO$_2$Me |
| G30 | D2 | Me | Et | —CH$_2$CH$_2$NHSO$_2$Me |
| G31 | D3 | Me | Et | —CH$_2$CH$_2$NHSO$_2$Me |
| G32 | D4 | Me | Et | —CH$_2$CH$_2$NHSO$_2$Me |
| G33 | D5 | Me | Et | —CH$_2$CH$_2$NHSO$_2$Me |
| G34 | D6 | Me | Et | —CH$_2$CH$_2$NHSO$_2$Me |
| G35 | D7 | Me | Et | —CH$_2$CH$_2$NHSO$_2$Me |
| G36 | D8 | Me | Et | —CH$_2$CH$_2$NHSO$_2$Me |

Invention Dye G37

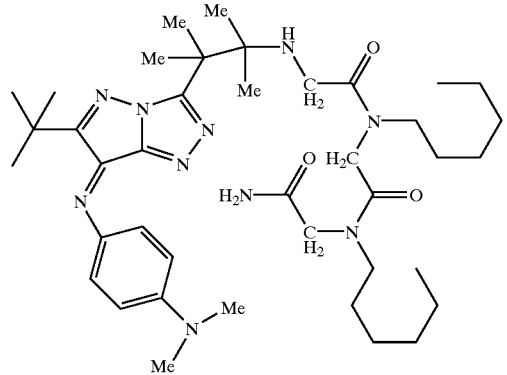

Invention Dye G38

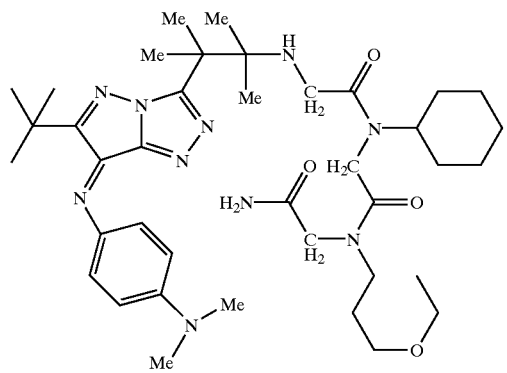

Invention Dye G39

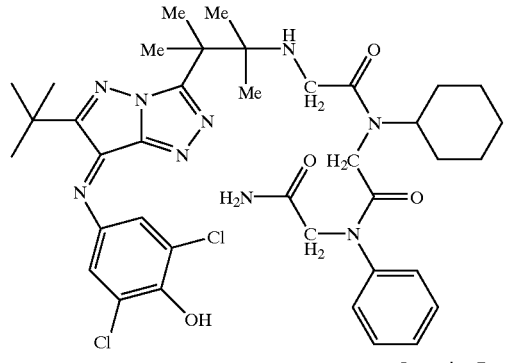

Invention Dye G40

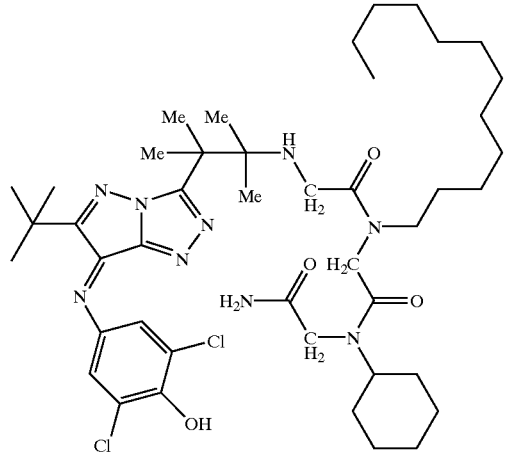

The couplers of this invention will be recognized by one skilled in the art as useful in photographic elements. The photographic elements of this invention can be single color elements or multicolor elements. Multicolor elements typically contain dye image-forming units sensitive to each of the three primary regions of the visible spectrum. Each unit can be comprised of a single emulsion layer or of multiple emulsion layers sensitive to a given region of the spectrum. The layers of the element, including the layers of the image-forming units, can be arranged in various orders as known in the art.

Unless otherwise specifically stated, use of the term "group", "substituted" or "substituent" means any group or atom other than hydrogen. Additionally, when the term "group" is used, it means that when a substituent group contains a substitutable hydrogen, it is also intended to encompass not only the substituent's unsubstituted form, but also its form further substituted with any substituent group or groups as herein mentioned, so long as the substituent does not destroy properties necessary for photographic utility. Suitably, a substituent group may be halogen or may be bonded to the remainder of the molecule by an atom of carbon, silicon, oxygen, nitrogen, phosphorous, or sulfur. The substituent may be, for example, halogen, such as chlorine, bromine or fluorine; nitro; hydroxyl; cyano; carboxyl; or groups which may be further substituted, such as alkyl, including straight or branched chain or cyclic alkyl, such as methyl, trifluoromethyl, ethyl, t-butyl, 3-(2,4-di-t-pentylphenoxy) propyl, cyclohexyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy) butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl)carbonylamino, p-dodecylphenylcarbonylamino, p-tolylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-tolylsulfonamido, p-dodecylbenzenesulfonamido, N-methyltetradecylsulfonamido, N,N-dipropyl-sulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl, N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

If desired, the substituents may themselves be further substituted one or more times with the described substituent groups. The particular substituents used may be selected by those skilled in the art to attain the desired photographic properties for a specific application and can include, for example, hydrophobic groups, solubilizing groups, blocking groups, and releasing or releasable groups. When a molecule may have two or more substituents, the substituents may be joined together to form a ring such as a fused ring unless otherwise provided. Generally, the above groups and substituents thereof may include those having up to 48 carbon atoms, typically 1 to 36 carbon atoms and usually less than 24 carbon atoms, but greater numbers are possible depending on the particular substituents selected.

The materials useful in the invention can be used in any of the ways and in any of the combinations known in the art. Typically, the invention materials are incorporated in a melt and coated as a layer described herein on a support to form part of a photographic element. When the term "associated" is employed, it signifies that a reactive compound is in or adjacent to a specified layer where, during processing, it is capable of reacting with other components.

To control the migration of various components, it may be desirable to include a high molecular weight hydrophobe or "ballast" group in coupler molecules. Representative ballast groups include substituted or unsubstituted alkyl or aryl groups containing 8 to 48 carbon atoms. Representative substituents on such groups include alkyl, aryl, alkoxy, aryloxy, alkylthio, hydroxy, halogen, alkoxycarbonyl, aryloxycarbonyl, carboxy, acyl, acyloxy, amino, anilino, carbonamido, carbamoyl, alkylsulfonyl, arylsulfonyl, sulfonamido, and sulfamoyl groups wherein the substituents typically contain 1 to 42 carbon atoms. Such substituents can also be further substituted.

The photographic elements can be single color elements or multicolor elements. Multicolor elements contain image dye-forming units sensitive to each of the three primary regions of the spectrum. Each unit can comprise a single emulsion layer or multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer.

A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler. The element can contain additional layers, such as filter layers, interlayers, overcoat layers, and subbing layers.

If desired, the photographic element can be used in conjunction with an applied magnetic layer as described in *Research Disclosure*, November 1992, Item 34390 published by Kenneth Mason Publications, Ltd., Dudley Annex, 12a North Street, Emsworth, Hampshire P010 7DQ, ENGLAND, and as described in Hatsumi Kyoukai Koukai Gihou No. 94-6023, published Mar. 15, 1994, available from the Japanese Patent Office. When it is desired to employ the inventive materials in a small format film, *Research Disclosure*, June 1994, Item 36230, provides suitable embodiments.

In the following discussion of suitable materials for use in the emulsions and elements of this invention, reference will be made to *Research Disclosure*, September 1996, Item 38957, available as described above, which is referred to herein by the term "Research Disclosure". The Sections hereinafter referred to are Sections of the Research Disclosure.

Except as provided, the silver halide emulsion containing elements employed in this invention can be either negative-working or positive-working as indicated by the type of processing instructions (i.e. color negative, reversal, or direct positive processing) provided with the element. Suitable emulsions and their preparation as well as methods of chemical and spectral sensitization are described in Sections I through V. Various additives such as UV dyes, brighteners, antifoggants, stabilizers, light absorbing and scattering materials, and physical property modifying addenda such as hardeners, coating aids, plasticizers, lubricants and matting agents are described, for example, in Sections II and VI through VIII. Color materials are described in Sections X through XIII. Suitable methods for incorporating couplers and dyes, including dispersions in organic solvents, are described in Section X(E). Scan facilitating is described in Section XIV. Supports, exposure, development systems, and processing methods and agents are described in Sections XV to XX. The information contained in the September 1994 *Research Disclosure*, Item No. 36544 referenced above, is updated in the September 1996 *Research Disclosure*, Item No. 38957. Certain desirable photographic elements and processing steps, including those useful in conjunction with color reflective prints, are described in *Research Disclosure*, Item 37038, February 1995.

Coupling-off groups are well known in the art. Such groups can determine the chemical equivalency of a coupler, i.e., whether it is a 2-equivalent or a 4-equivalent coupler, or modify the reactivity of the coupler. Such groups can advantageously affect the layer in which the coupler is coated, or other layers in the photographic recording material, by performing, after release from the coupler, functions such as dye formation, dye hue adjustment, development acceleration or inhibition, bleach acceleration or inhibition, electron transfer facilitation, and color correction.

The presence of hydrogen at the coupling site provides a 4-equivalent coupler, and the presence of another coupling-off group usually provides a 2-equivalent coupler. Representative classes of such coupling-off groups include, for example, chloro, alkoxy, aryloxy, hetero-oxy, sulfonyloxy, acyloxy, acyl, heterocyclyl, sulfonamido, mercaptotetrazole, benzothiazole, mercaptopropionic acid, phosphonyloxy, arylthio, and arylazo. These coupling-off groups are described in the art, for example, in U.S. Pat. Nos. 2,455,169, 3,227,551, 3,432,521, 3,476,563, 3,617,291, 3,880,661, 4,052,212 and 4,134,766; and in UK. Patents and published application Nos. 1,466,728, 1,531,927, 1,533,039, 2,006, 755A and 2,017,704A.

Image dye-forming couplers may be included in the element such as couplers that form cyan dyes upon reaction with oxidized color developing agents which are described in such representative patents and publications as: "Farbkuppler-eine Literature Ubersicht," published in Agfa Mitteilungen, Band III, pp. 156–175 (1961) as well as in U.S. Pat. Nos. 2,367,531; 2,423,730; 2,474,293; 2,772,162; 2,895,826; 3,002,836; 3,034,892; 3,041,236; 4,333,999; 4,746,602; 4,753,871; 4,770,988; 4,775,616; 4,818,667; 4,818,672; 4,822,729; 4,839,267; 4,840,883; 4,849,328; 4,865,961; 4,873,183; 4,883,746; 4,900,656; 4,904,575; 4,916,051; 4,921,783; 4,923,791; 4,950,585; 4,971,898; 4,990,436; 4,996,139; 5,008,180; 5,015,565; 5,011,765; 5,011,766; 5,017,467; 5,045,442; 5,051,347; 5,061,613; 5,071,737; 5,075,207; 5,091,297; 5,094,938; 5,104,783; 5,178,993; 5,813,729; 5,187,057; 5,192,651; 5,200,305; 5,202,224; 5,206,130; 5,208,141; 5,210,011; 5,215,871; 5,223,386; 5,227,287; 5,256,526; 5,258,270; 5,272,051; 5,306,610; 5,326,682; 5,366,856; 5,378,596; 5,380,638; 5,382,502; 5,384,236; 5,397,691; 5,415,990; 5,434,034; 5,441,863; EPO 0 246 616; EPO 0 250 201; EPO 0 271 323; EPO 0 295 632; EPO 0 307 927; EPO 0 333 185; EPO 0 378 898; EPO 0 389 817; EPO 0 487 111; EPO 0 488 248; EPO 0 539 034; EPO 0 545 300; EPO 0 556 700; EPO 0 556 777; EPO 0 556 858; EPO 0 569 979; EPO 0 608 133; EPO 0 636 936; EPO 0 651 286; EPO 0 690 344; German OLS 4,026,903; German OLS 3,624,777. and German OLS 3,823,049. Typically such couplers are phenols, naphthols, or pyrazoloazoles.

Couplers that form magenta dyes upon reaction with oxidized color developing agent are described in such representative patents and publications as: "Farbkuppler-eine Literature Ubersicht," published in Agfa Mitteilungen, Band III, pp. 126–156 (1961) as well as U.S. Pat. Nos. 2,311,082 and 2,369,489; 2,343,701; 2,600,788; 2,908,573; 3,062,653; 3,152,896; 3,519,429; 3,758,309; 3,935,015; 4,540,654; 4,745,052; 4,762,775; 4,791,052; 4,812,576; 4,835,094; 4,840,877; 4,845,022; 4,853,319; 4,868,099; 4,865,960; 4,871,652; 4,876,182; 4,892,805; 4,900,657; 4,910,124; 4,914,013; 4,921,968; 4,929,540; 4,933,465; 4,942,116; 4,942,117; 4,942,118; U.S. Pat. Nos. 4,959,480; 4,968,594; 4,988,614; 4,992,361; 5,002,864; 5,021,325; 5,066,575; 5,068,171; 5,071,739; 5,100,772; 5,110,942; 5,116,990; 5,118,812; 5,134,059; 5,155,016; 5,183,728; 5,234,805;

5,235,058; 5,250,400; 5,254,446; 5,262,292; 5,300,407; 5,302,496; 5,336,593; 5,350,667; 5,395,968; 5,354,826; 5,358,829; 5,368,998; 5,378,587; 5,409,808; 5,411,841; 5,418,123; 5,424,179; EPO 0 257 854; EPO 0 284 240; EPO 0 341 204; EPO 347,235; EPO 365,252; EPO 0 422 595; EPO 0 428 899; EPO 0 428 902; EPO 0 459 331; EPO 0 467 327; EPO 0 476 949; EPO 0 487 081; EPO 0 489 333; EPO 0 512 304; EPO 0 515 128; EPO 0 534 703; EPO 0 554 778; EPO 0 558 145; EPO 0 571 959; EPO 0 583 832; EPO 0 583 834; EPO 0 584 793; EPO 0 602 748; EPO 0 602 749; EPO 0 605 918; EPO 0 622 672; EPO 0 622 673; EPO 0 629 912; EPO 0 646 841, EPO 0 656 561; EPO 0 660 177; EPO 0 686 872; WO 90/10253; WO 92/09010; WO 92/10788; WO 92/12464; WO 93/01523; WO 93/02392; WO 93/02393; WO 93/07534; UK Application 2,244,053; Japanese Application 03192-350; German OLS 3,624,103; German OLS 3,912,265; and German OLS 40 08 067. Typically such couplers are pyrazolones, pyrazoloazoles, or pyrazolobenzimidazoles that form magenta dyes upon reaction with oxidized color developing agents.

Couplers that form yellow dyes upon reaction with oxidized color developing agent are described in such representative patents and publications as: "Farbkuppler-eine Literature Ubersicht," published in Agfa Mitteilungen; Band III; pp. 112–126 (1961); as well as U.S. Pat. Nos. 2,298,443; 2,407,210; 2,875,057; 3,048,194; 3,265,506; 3,447,928; 4,022,620; 4,443,536; 4,758,501; 4,791,050; 4,824,771; 4,824,773; 4,855,222; 4,978,605; 4,992,360; 4,994,361; 5,021,333; 5,053,325; 5,066,574; 5,066,576; 5,100,773; 5,118,599; 5,143,823; 5,187,055; 5,190,848; 5,213,958; 5,215,877; 5,215,878; 5,217,857; 5,219,716; 5,238,803; 5,283,166; 5,294,531; 5,306,609; 5,328,818; 5,336,591; 5,338,654; 5,358,835; 5,358,838; 5,360,713; 5,362,617; 5,382,506; 5,389,504; 5,399,474; 5,405,737; 5,411,848; 5,427,898; EPO 0 327 976; EPO 0 296 793; EPO 0 365 282; EPO 0 379 309; EPO 0 415 375; EPO 0 437 818; EPO 0 447 969; EPO 0 542 463; EPO 0 568 037; EPO 0 568 196; EPO 0 568 777; EPO 0 570 006; EPO 0 573 761; EPO 0 608 956; EPO 0 608 957; and EPO 0 628 865. Such couplers are typically open chain ketomethylene compounds.

Couplers that form colorless products upon reaction with oxidized color developing agent are described in such representative patents as: UK. 861,138; U.S. Pat. Nos. 3,632, 345; 3,928,041; 3,958,993 and 3,961,959. Typically such couplers are cyclic carbonyl containing compounds that form colorless products on reaction with an oxidized color developing agent.

Couplers that form black dyes upon reaction with oxidized color developing agent are described in such representative patents as U.S. Pat. Nos. 1,939,231; 2,181,944; 2,333,106; and 4,126,461; German OLS No. 2,644,194 and German OLS No. 2,650,764. Typically, such couplers are resorcinols or m-aminophenols that form black or neutral products on reaction with oxidized color developing agent.

In addition to the foregoing, so-called "universal" or "washout" couplers may be employed. These couplers do not contribute to image dye-formation. Thus, for example, a naphthol having an unsubstituted carbamoyl or one substituted with a low molecular weight substituent at the 2- or 3-position may be employed. Couplers of this type are described, for example, in U.S. Pat. Nos. 5,026,628, 5,151, 343, and 5,234,800.

It may be useful to use a combination of couplers any of which may contain known ballasts or coupling-off groups such as those described in U.S. Pat. No. 4,301,235; U.S. Pat. No. 4,853,319 and U.S. Pat. No. 4,351,897. The coupler may contain solubilizing groups such as described in U.S. Pat. No. 4,482,629. The coupler may also be used in association with "wrong" colored couplers (e.g. to adjust levels of interlayer correction) and, in color negative applications, with masking couplers such as those described in EP 213.490; Japanese Published Application 58-172,647; U.S. Pat. Nos. 2,983,608; 4,070,191; and 4,273,861; German Applications DE 2,706,117 and DE 2,643,965; UK. Patent 1,530,272; and Japanese Application 58-113935. The masking couplers may be shifted or blocked, if desired.

Typically, couplers are incorporated in a silver halide emulsion layer in a mole ratio to silver of 0.05 to 1.0 and generally 0.1 to 0.5. Usually the couplers are dispersed in a high-boiling organic solvent in a weight ratio of solvent to coupler of 0.1 to 10.0 and typically 0.1 to 2.0 although dispersions using no permanent coupler solvent are sometimes employed.

The invention may be used in association with materials that release Photographically Useful Groups (PUGS) that accelerate or otherwise modify the processing steps e.g. of bleaching or fixing to improve the quality of the image. Bleach accelerator releasing couplers such as those described in EP 193,389; EP 301,477; U.S. Pat. No. 4,163, 669; U.S. Pat. No. 4,865,956; and U.S. Pat. No. 4,923,784, may be useful. Also contemplated is use in association with nucleating agents, development accelerators or their precursors (UK Patent 2,097,140; UK. Patent 2,131,188); electron transfer agents (U.S. Pat. No. 4,859,578; U.S. Pat. No. 4,912,025); antifogging and anti color-mixing agents such as derivatives of hydroquinones, aminophenols, amines, gallic acid; catechol; ascorbic acid; hydrazides; sulfonamidophenols; and non color-forming couplers.

The invention may also be used in combination with filter dye layers comprising colloidal silver sol or yellow, cyan, and/or magenta filter dyes, either as oil-in-water dispersions, latex dispersions or as solid particle dispersions. Additionally, they may be used with "smearing" couplers (e.g. as described in U.S. Pat. No. 4,366,237; EP 96,570; U.S. Pat. No. 4,420,556; and U.S. Pat. No. 4,543,323.) Also, the materials useful in the invention may be blocked or coated in protected form as described, for example, in Japanese Application 61/258,249 or U.S. Pat. No. 5,019, 492.

The invention may further be used in combination with image-modifying compounds that release PUGS such as "Developer Inhibitor-Releasing" compounds (DIR's). DIR's useful in conjunction with the invention are known in the art and examples are described in U.S. Pat. Nos. 3,137, 578; 3,148,022; 3,148,062; 3,227,554; 3,384,657; 3,379, 529; 3,615,506; 3,617,291; 3,620,746; 3,701,783; 3,733, 201; 4,049,455; 4,095,984; 4,126,459; 4,149,886; 4,150, 228; 4,211,562; 4,248,962; 4,259,437; 4,362,878; 4,409, 323; 4,477,563; 4,782,012; 4,962,018; 4,500,634; 4,579, 816; 4,607,004; 4,618,571; 4,678,739; 4,746,600; 4,746, 601; 4,791,049; 4,857,447; 4,865,959; 4,880,342; 4,886, 736; 4,937,179; 4,946,767; 4,948,716; 4,952,485; 4,956, 269; 4,959,299; 4,966,835; 4,985,336 as well as in patent publications GB 1,560,240; GB 2,007,662; GB 2,032,914; GB 2,099,167; DE 2,842,063, DE 2,937,127; DE 3,636,824; DE 3,644,416 as well as the following European Patent Publications: 272,573; 335,319; 336,411; 346, 899; 362, 870; 365,252; 365,346; 373,382; 376,212; 377,463; 378, 236; 384,670; 396,486; 401,612; 401,613.

Such compounds are also disclosed in "Developer-Inhibitor-Releasing (DIR) Couplers for Color Photography," C. R. Barr, J. R. Thirtle and P. W. Vittum in *Photographic Science and Engineering*, Vol. 13, p. 174 (1969). Generally, the developer inhibitor-releasing (DIR) couplers include a coupler moiety and an inhibitor coupling-off moiety (IN). The inhibitor-releasing couplers may be of the time-delayed type (DIAR couplers) which also include a timing moiety or chemical switch which produces a delayed release of inhibitor. Examples of typical inhibitor moieties are: oxazoles, thiazoles, diazoles, triazoles, oxadiazoles, thiadiazoles, oxathiazoles, thiatriazoles, benzotriazoles, tetrazoles, benzimidazoles, indazoles, isoindazoles, mercaptotetrazoles, selenotetrazoles, mercaptobenzothiazoles, selenobenzothiazoles, mercaptobenzoxazoles, selenobenzoxazoles, mercaptobenzimidazoles, selenobenzimidazoles, benzodiazoles, mercaptooxazoles, mercaptothiadiazoles, mercaptothiazoles, mercaptotriazoles, mercaptooxadiazoles, mercaptodiazoles, mercaptooxathiazoles, telleurotetrazoles or benzisodiazoles. In a preferred embodiment, the inhibitor moiety or group is selected from the following formulas:

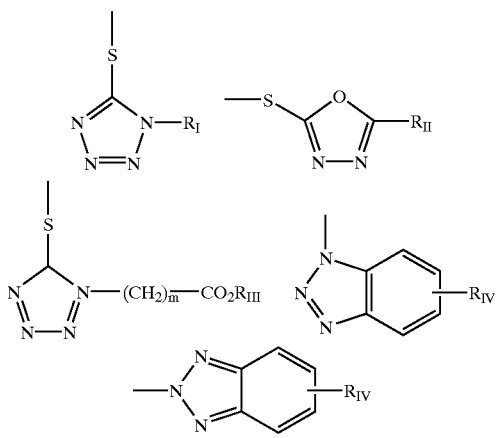

wherein $R_I$ is selected from the group consisting of straight and branched alkyls of from 1 to about 8 carbon atoms, benzyl, phenyl, and alkoxy groups and such groups containing none, one or more than one such substituent; $R_{II}$ is selected from $R_I$ and —$SR_I$; $R_{III}$ is a straight or branched alkyl group of from 1 to about 5 carbon atoms and m is from 1 to 3; and $R_{IV}$ is selected from the group consisting of hydrogen, halogens and alkoxy, phenyl and carbonamido groups, —$COOR_V$ and —$NHCOOR_V$ wherein $R_V$ is selected from substituted and unsubstituted alkyl and aryl groups.

Although it is typical that the coupler moiety included in the developer inhibitor-releasing coupler forms an image dye corresponding to the layer in which it is located, it may also form a different color as one associated with a different film layer. It may also be useful that the coupler moiety included in the developer inhibitor-releasing coupler forms colorless products and/or products that wash out of the photographic material during processing (so-called "universal" couplers).

A compound such as a coupler may release a PUG directly upon reaction of the compound during processing, or indirectly through a timing or linking group. A timing group produces the time-delayed release of the PUG such groups using an intramolecular nucleophilic substitution reaction (U.S. Pat. No. 4,248,962); groups utilizing an electron transfer reaction along a conjugated system (U.S. Pat. Nos. 4,409,323; 4,421,845; 4,861,701, Japanese Applications 57-188035; 58-98728; 58-209736; 58-209738); groups that function as a coupler or reducing agent after the coupler reaction (U.S. Pat. No. 4,438,193; U.S. Pat. No. 4,618,571) and groups that combine the features describe above. It is typical that the timing group is of one of the formulas:

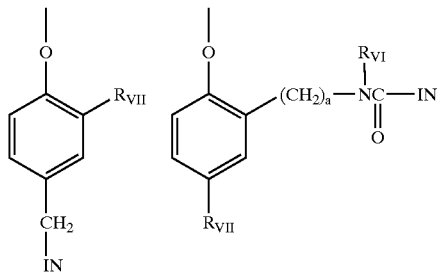

wherein IN is the inhibitor moiety, $R_{VII}$ is selected from the group consisting of nitro, cyano, alkylsulfonyl; sulfamoyl; and sulfonamido groups; a is 0 or 1; and $R_{VI}$ is selected from the group consisting of substituted and unsubstituted alkyl and phenyl groups. The oxygen atom of each timing group is bonded to the coupling-off position of the respective coupler moiety of the DIAR.

The timing or linking groups may also function by electron transfer down an unconjugated chain. Linking groups are known in the art under various names. Often they have been referred to as groups capable of utilizing a hemiacetal or iminoketal cleavage reaction or as groups capable of utilizing a cleavage reaction due to ester hydrolysis such as U.S. Pat. No. 4,546,073. This electron transfer down an unconjugated chain typically results in a relatively fast decomposition and the production of carbon dioxide, formaldehyde, or other low molecular weight by-products. The groups are exemplified in EP 464,612, EP 523,451, U.S. Pat. No. 4,146,396, Japanese Kokai 60-249148 and 60-249149.

Suitable developer inhibitor-releasing couplers for use in the present invention include, but are not limited to, the following:

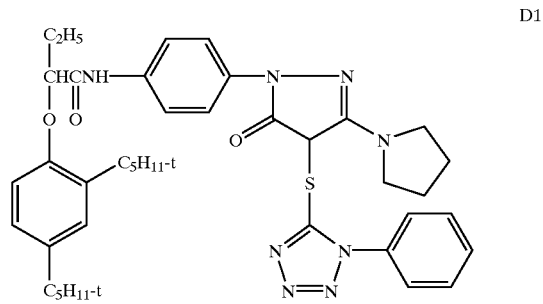

D1

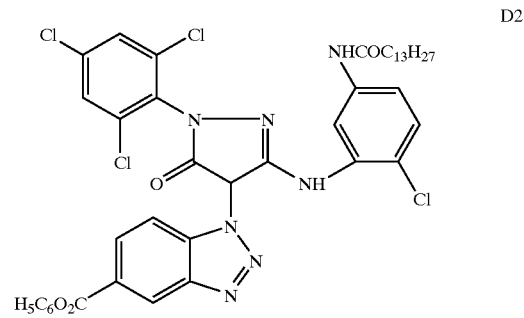

D2

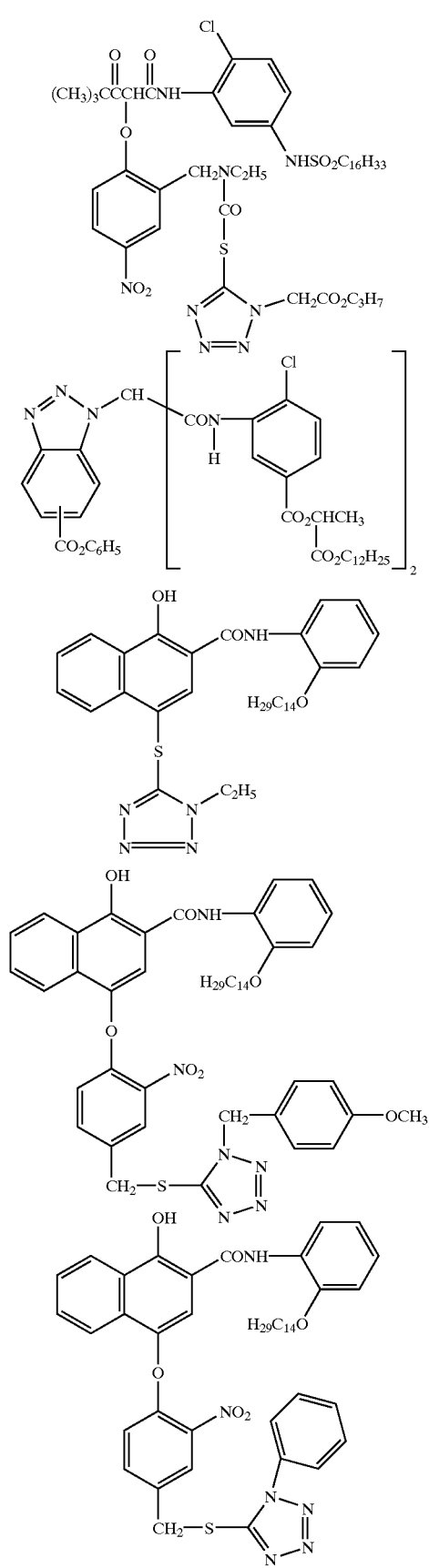
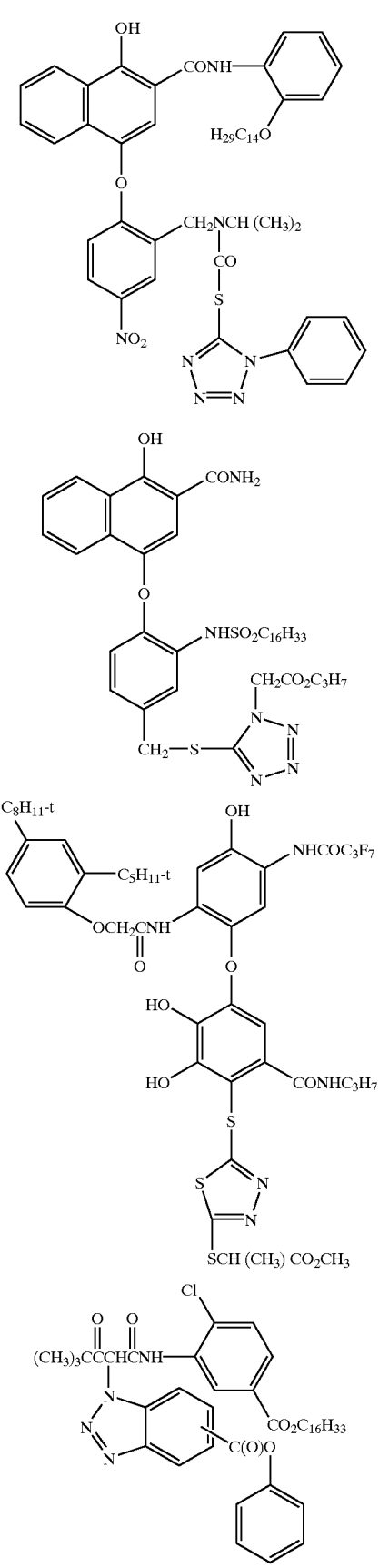

-continued

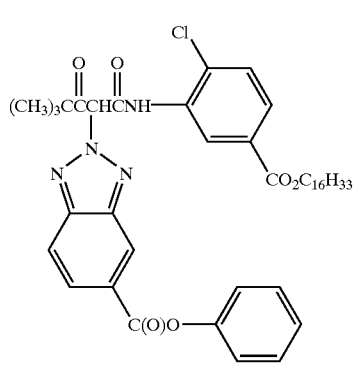

D12

It is also contemplated that the present invention may be employed to obtain reflection color prints as described in *Research Disclosure*, November 1979, Item 18716, available from Kenneth Mason Publications, Ltd, Dudley Annex, 12a North Street, Emsworth, Hampshire P0101 7DQ, England. Materials useful in the invention may be coated on pH adjusted support as described in U.S. Pat. No. 4,917,994; on a support with reduced oxygen permeability (EP 553, 339); with epoxy solvents (EP 164,961); with nickel complex stabilizers (U.S. Pat. No. 4,346,165; U.S. Pat. No. 4,540,653 and U.S. Pat. No. 4,906,559 for example); with ballasted chelating agents such as those in U.S. Pat. No. 4,994,359 to reduce sensitivity to polyvalent cations such as calcium; and with stain reducing compounds such as described in U.S. Pat. No. 5,068,171. Other compounds useful in combination with the invention are disclosed in Japanese Published Applications described in Derwent Abstracts having accession numbers as follows: 90-072,629, 90-072,630; 90-072,631; 90-072,632; 90-072,633; 90-072,634; 90-077,822; 90-078,229; 90-078,230; 90-079,336; 90-079,337; 90-079,338; 90-079,690; 90-079,691; 90-080,487; 90-080,488; 90-080,489; 90-080,490; 90-080,491; 90-080,492; 90-080,494; 90-085,928; 90-086,669; 90-086,670; 90-087,360; 90-087,361; 90-087,362; 90-087,363; 90-087,364; 90-088,097; 90-093,662; 90-093,663; 90-093,664; 90-093,665; 90-093,666; 90-093,668; 90-094,055; 90-094,056; 90-103,409; 83-62,586; 83-09,959.

Conventional radiation-sensitive silver halide emulsions can be employed in the practice of this invention. Such emulsions are illustrated by *Research Disclosure*, Item 38755, September 1996, I. Emulsion grains and their preparation.

Especially useful in this invention are tabular grain silver halide emulsions. Tabular grains are those having two parallel major crystal faces and having an aspect ratio of at least 2. The term "aspect ratio" is the ratio of the equivalent circular diameter (ECD) of a grain major face divided by its thickness (t). Tabular grain emulsions are those in which the tabular grains account for at least 50 percent (preferably at least 70 percent and optimally at least 90 percent) of the total grain projected area. Preferred tabular grain emulsions are those in which the average thickness of the tabular grains is less than 0.3 micrometer (preferably thin—that is, less than 0.2 micrometer and most preferably ultrathin—that is, less than 0.07 micrometer). The major faces of the tabular grains can lie in either {111} or {100} crystal planes. The mean ECD of tabular grain emulsions rarely exceeds 10 micrometers and more typically is less than 5 micrometers.

In their most widely used form tabular grain emulsions are high bromide {111} tabular grain emulsions. Such emulsions are illustrated by Kofron et al U.S. Pat. No. 4,439,520, Wilgus et al U.S. Pat. No. 4,434,226, Solberg et al U.S. Pat. No. 4,433,048, Maskasky U.S. Pat. Nos. 4,435,501, 4,463,087 and 4,173,320, Daubendiek et al U.S. Pat. Nos. 4,414,310 and 4,914,014, Sowinski et al U.S. Pat. No. 4,656,122, Piggin et al U.S. Pat. Nos. 5,061,616 and 5,061,609, Tsaur et al U.S. Pat. Nos. 5,147,771, '772, '773, 5,171,659 and 5,252,453, Black et al 5,219,720 and 5,334,495, Delton U.S. Pat. Nos. 5,310,644, 5,372,927 and 5,460,934, Wen U.S. Pat. No. 5,470,698, Fenton et al U.S. Pat. No. 5,476,760, Eshelman et al U.S. Pat. Nos. 5,612,175 and 5,614,359, and Irving et al U.S. Pat. No. 5,667,954.

Ultrathin high bromide {111} tabular grain emulsions are illustrated by Daubendiek et al U.S. Pat. Nos. 4,672,027, 4,693,964, 5,494,789, 5,503,971 and 5,576,168, Antoniades et al U.S. Pat. No. 5,250,403, Olm et al U.S. Pat. No. 5,503,970, Deaton et al U.S. Pat. No. 5,582,965, and Maskasky U.S. Pat. No. 5,667,955.

High bromide {100} tabular grain emulsions are illustrated by Mignot U.S. Pat. Nos. 4,386,156 and 5,386,156.

High chloride {111} tabular grain emulsions are illustrated by Wey U.S. Pat. No. 4,399,215, Wey et al U.S. Pat. No. 4,414,306, Maskasky U.S. Pat. Nos. 4,400,463, 4,713,323, 5,061,617, 5,178,997, 5,183,732, 5,185,239, 5,399,478 and 5,411,852, and Maskasky et al U.S. Pat. Nos. 5,176,992 and 5,178,998. Ultrathin high chloride {111} tabular grain emulsions are illustrated by Maskasky U.S. Pat. Nos. 5,271,858 and 5,389,509.

High chloride {100} tabular grain emulsions are illustrated by Maskasky U.S. Pat. Nos. 5,264,337, 5,292,632, 5,275,930 and 5,399,477, House et al U.S. Pat. No. 5,320,938, Brust et al U.S. Pat. No. 5,314,798, Szajewski et al U.S. Pat. No. 5,356,764, Chang et al U.S. Pat. Nos. 5,413,904 and 5,663,041, Oyamada U.S. Pat. No. 5,593,821, Yamashita et al U.S. Pat. Nos. 5,641,620 and 5,652,088, Saitou et al U.S. Pat. No. 5,652,089, and Oyamada et al U.S. Pat. No. 5,665,530. Ultrathin high chloride {100} tabular grain emulsions can be prepared by nucleation in the presence of iodide, following the teaching of House et al and Chang et al, cited above.

The emulsions can be surface-sensitive emulsions, i.e., emulsions that form latent images primarily on the surfaces of the silver halide grains, or the emulsions can form internal latent images predominantly in the interior of the silver halide grains. The emulsions can be negative-working emulsions, such as surface-sensitive emulsions or unfogged internal latent image-forming emulsions, or direct-positive emulsions of the unfogged, internal latent image-forming type, which are positive-working when development is conducted with uniform light exposure or in the presence of a nucleating agent. Tabular grain emulsions of the latter type are illustrated by Evans et al. U.S. Pat. No. 4,504,570.

Photographic elements can be exposed to actinic radiation, typically in the visible region of the spectrum, to form a latent image and can then be processed to form a visible dye image. Processing to form a visible dye image includes the step of contacting the element with a color-developing agent to reduce developable silver halide and oxidize the color-developing agent. Oxidized color developing agent in turn reacts with the coupler to yield a dye. If desired "Redox Amplification" as described in Research Disclosure XVIIIB(5) may be used.

A "color negative element" utilizes negative-working silver halide and provides a negative image upon processing. A first type of such element is a capture element, which is a color negative film that is designed for capturing an image in negative form rather than for viewing an image. A second type of such an element is a direct-view element that is designed, at least in part, for providing a positive image viewable by humans.

In the capture element, speed (the sensitivity of the element to low light conditions) is usually critical to obtaining sufficient image in such elements. Such elements are typically silver bromoiodide emulsions coated on a transparent support and are sold packaged with instructions to process in known color negative processes such as the Kodak C-41 process as described in The British Journal of Photography Annual of 1988, pages 191–198. If a color negative film element is to be subsequently employed to generate a viewable projection print as for a motion picture, a process such as the Kodak ECN-2 process described in the H-24 Manual available from Eastman Kodak Co. may be employed to provide the color negative image on a transparent support. Color negative development times are typically 3' 15" or less and desirably 90 or even 60 seconds or less.

A direct-view photographic element is one which yields a color image that is designed for human viewing (1) by reflected light, such as a photographic paper print, (2) by transmitted light, such as a display transparency, or (3) by projection, such as a color slide or a motion picture print. These direct-view elements may be exposed and processed in a variety of ways. For example, paper prints, display transparencies, and motion picture prints are typically produced by digitally printing or by optically printing an image from a color negative onto the direct-viewing element and processing though an appropriate negative-working photographic process to give a positive color image. The element may be sold packaged with instructions for digital printing or for processing using a color negative optical printing process, for example the Kodak RA-4 process, as generally described in PCT WO 87/04534 or U.S. Pat. No. 4,975,357, to form a positive image. Color projection prints may be processed, for example, in accordance with the Kodak ECP-2 process as described in the H-24 Manual. Color print development times are typically 90 seconds or less and desirably 45 or even 30 seconds or less. Color slides may be produced in a similar manner but are more typically produced by exposing the film directly in a camera and processing through a reversal color process or a direct positive process to give a positive color image. The foregoing images may also be produced by alternative processes such as digital printing.

Each of these types of photographic elements has its own particular requirements for dye hue, but in general they all require cyan dyes whose absorption bands are less deeply absorbing (that is, shifted away from the red end of the spectrum) than color negative films. This is because dyes in direct-view elements are selected to have the best appearance when viewed by human eyes, whereas the dyes in image capture materials are designed to best match the needs of the printing process.

A reversal element is capable of forming a positive image without optical printing. To provide a positive (or reversal) image, the color development step is preceded by development with a non-chromogenic developing agent to develop exposed silver halide, but not form dye, and followed by uniformly fogging the element to render unexposed silver halide developable. Such reversal elements are typically sold packaged with instructions to process using a color reversal process such as the Kodak E-6 process as described in The British Journal of Photography Annual of 1988, page 194. Alternatively, a direct positive emulsion can be employed to obtain a positive image.

The above elements are typically sold with instructions to process using the appropriate method such as the mentioned color negative (Kodak C-41), color print (Kodak RA-4), or reversal (Kodak E-6) process.

The photographic element of the invention can be incorporated into exposure structures intended for repeated use or exposure structures intended for limited use, variously referred to by names such as "single use cameras", "lens with film", or "photosensitive material package units".

Preferred color developing agents are p-phenylenediamines such as:

4-amino-N,N-diethylaniline hydrochloride, 4-amino-3-methyl-N,N-diethylaniline hydrochloride, 4-amino-3-methyl-N-ethyl-N-(2-methanesulfonamidoethyl) aniline sesquisulfate hydrate, 4-amino-3-methyl-N-ethyl-N-(2-hydroxyethyl)aniline sulfate, 4-amino-3-(2-methanesulfonamidoethyl)-N,N-diethylaniline hydrochloride, and 4-amino-N-ethyl-N-(2-methoxyethyl)-m-toluidine di-p-toluene sulfonic acid.

Development is usually followed by the conventional steps of bleaching, fixing, or bleach-fixing, to remove silver or silver halide, washing, and drying.

Synthesis

The synthesis of oligomeric N-substituted glycines has been described by R. N. Zuckermann, et. al., *J. Am. Chem. Soc.*, 1992, 10646–10647; and *J. Med. Chem.* 1994, 2678–2685, by Eric M. Gordon and James F. Kerwin, Jr., *Combinatorial Chemistry and Molecular Diversity in Drug Discovery*, Wiley-Liss Press, John Wiley and Sons, Inc. New York, N.Y., 1998, by Barry A. Bunin, *The Combinatorial Index*, Academic Press, New York, 1998, and by Anthony W. Czarnik and Sheila DeWitt, *A Practical Guide to Combinatorial Chemistry*, ACS Professional Reference Books, Washington, D.C., 1997. These materials have been named peptoids because they are structurally related to the well known peptides. Further, S. M. Miller, et. al., *Bioorganic & Medicinal Chemistry Lett.*, 1994, 2657–2662, has reported that N-substituted glycines are less rapidly hydrolyzed than similar L-amino containing peptides. Further it is anticipated that the unwanted hydrogen bonding of peptide linkages resulting in excessive aqueous solubility and crystallinity would be greatly diminished by introduction of a substituent on the nitrogen of the glycine fragment resulting in overall higher hydrophobicity which is a desirable characteristic of oil soluble imaging dyes. Peptoid substituted pyrazoloazole couplers may be synthesized by using a substituted pyrazoloazole in which the substituent on a carbon center contains a primary amine functional group.

Couplers of the present invention can be prepared by simple reactions and methods described below. U.S. Pat. No. 5,256,526 provides useful intermediates for pyrrolotriazoles. Typical syntheses are illustrated by the following examples. In the examples below the starting material Rink Amide Resin, RAR, is commercially available from Argonaut Technologies, Inc., San Carlos, Calif., U.S.A. and is sold as the FMOC protected material under the name of "PS-Rink-Fmoc Resin". This resin is a polystyrene backbone lightly (1–2%) cross-linked with divinylbenzene that has been functionalized with 4-(2,4-dimethoxyphenyl-Fmoc-aminomethyl)-phenylacetic acid, where the Fmoc group is 9-fluorenylmethyloxycarbonyl. The typical bead size is 90–105 microns and the typical amine loading is 0.90–0.95 mmol per gram. Similar Rink Amide Resins may also be sold from the same supplier under the trade names of Argogel™ and Argopore™ and will have bead size and amine loading which is different than "PS-Rink-Fmoc Resin". All described reactions were run in an Argonaut Quest 210™ TM Reactor using 5 mL Teflon reaction vessels which allowed for the simultaneous synthesis of up to twenty materials. It will be understood by one skilled in the art of organic synthesis that the reactions could also be carried out using conventional laboratory glassware with the expectation that similar results would be obtained.

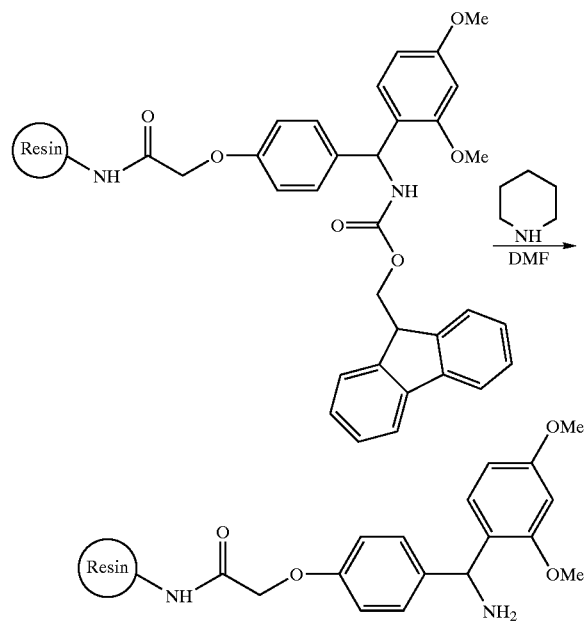

General Procedure Rink-NH-Fmoc Resin to Rink-NH$_2$ Resin

Into a 5 mL reaction vessel was placed 0.2 grams of PS-Rink-Fmoc Resin. The resin was swelled by the addition of 4 mL of dimethylformamide. The resin was agitated for 10 minutes and then the reaction vessel drained. The 9-fluorenylmethyloxycarbonyl (Fmoc) group was removed by treatment with 4 mL of a stock solution of 20% piperidine in dimethylformamide (volume %), agitated for 5 minutes, then the vessel was drained. This treatment with 20% piperidine in dimethylformamide was repeated once more. The resin was then washed four times each with 4 mL of dimethylformamide, dichloromethane, tetrahydrofuran and finally with dimethylformamide again with 3 minutes agitation during each wash. The resin was air dried, and a sample removed from the reaction vessel and analyzed for percent Fmoc removal by NMR which showed complete removal of the Fmoc group.

EXAMPLE 1

Synthesis of Coupler A1

Step 1. Into a 5 mL reaction vessel containing 0.2 grams of Rink-NH2 resin, described above, was added 3 mL of 0.6 Molar solution of bromoacetic acid in dimethylformamide and 1 mL of 3.2 Molar solution of diisopropylcarbodiimide in dimethylformamide. The vessel contents were mixed at room temperature for 30 minutes, drained and the operation repeated twice more. The resin was then washed four times each with 4 mL of dimethylformamide and 4 mL of dimethylsulfoxide with 2.5 minutes agitation during each wash. After draining the wash solvent, a 4 mL solution of 2.0 Molar cyclohexylamine in dimethylsulfoxide was added. The resin reaction mixture was agitated for 18 hours at room temperature then drained. The resin was then washed eight times with 4 mL dimethylformamide each for 2.5 minutes agitation.

Step 2. After draining the wash solvent, was added 3 mL of 0.6 Molar solution of bromoacetic acid in dimethylformamide and 1 mL of 3.2 Molar solution of diisopropylcarbodiimide in dimethylformamide. The vessel contents were mixed for 30 minutes, drained and the operation repeated twice more. The resin was then washed four times each with 4 mL of dimethylformamide and 4 mL of dimethylsulfoxide with 2.5 minutes agitation during each wash. After draining the wash solvent, was added 4 mL of a 0.5 Molar dichloromethane, or optionally dimethylsulfoxide, solution of 6-(1,1-dimethylethyl)-α,α,β,β-tetramethyl-1H-pyrazolo[5,1-c]-1,2,4-triazole-3-ethanamine, Chemical Abstracts Registry Number 210405-85-9 whose preparation has been described in Harder, et. al., U.S. Pat. No. 5,925,503 (July 1999). The resin reaction mixture was agitated for 18 hours at room temperature then drained. The resin was then thoroughly washed four times each with 4 mL of dimethylformamide, tetrahydrofuran, methanol and dichloromethane with 2.5 minutes agitation during each wash. This process was repeated twice.

Step 3. After draining the wash solvent, the product was cleaved from the resin by treatment with 4 mL of 20% trifluoroacetic acid in dichloromethane (volume %), agitation for 30 min, then draining with collection of the cleavage solution containing product. This operation was repeated twice more and the collected cleavage solutions were combined. The resin was then washed three times with 4 mL of dichloromethane and this solvent was also added to the cleavage solution containing product. The cleavage solution was then concentrated to dryness under vacuum without heat to afford 117 milligrams of product A1 with 84% purity as determined by Reverse Phase High Pressure Liquid Chromatography analysis. Electrospray MS: [MH]+=460 m/e.

Using the above procedure with substitution of 2-ethylhexylamine, dodecylamine, 3-ethoxypropylamine,

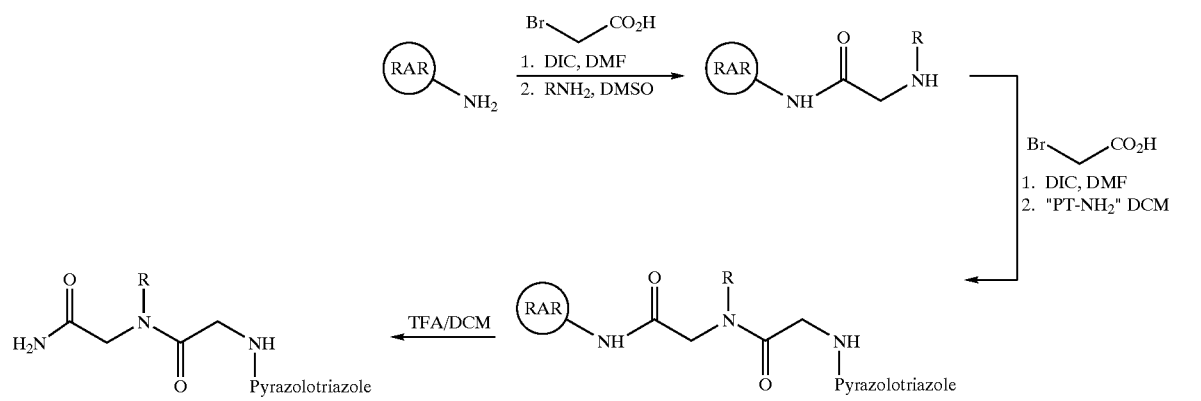

cyclohexanemethylamine, benzylamine, aniline or 1-(3-aminopropyl)-2-pyrrolidinone, and hexylamine all available from the Aldrich Chemical Company, Milwaukee, Wis., U.S.A., for cyclohexylamine the peptoid couplers A2–A8 could be obtained. Product weight, product purity and Electrospray mass spectrum [MH]+ ion are shown in Table I for couplers A1–A3.

Using the above procedure with substitution of 6-(1,1-dimethylethyl)-pyrazolo[5,1-c]-1,2,4-triazole-3-ethanamine, whose preparation as the toluenesulfonic acid salt, Chemical Abstract Registry Number 152602-81-8, is described in Kirschke, et. al., *Liebigs Ann. Chem.* 1994, 10, 1037–42, for 6-(1,1-dimethylethyl)-α,α,β,β-tetramethyl-1H-pyrazolo[5,1-c]-1,2,4-triazole-3-ethanamine, the peptoid couplers A'1–A'8 could be obtained.

Using the above procedure with substitution of 6-(1,1-dimethylethyl)-β-methyl-pyrazolo[1,5-b]-1,2,4-triazole-2-ethanamine, Chemical Abstract Registry Number 180483-99-2, whose preparation is described in Kawagishi, T., et. al., U.S. Pat. No. 5,605,788, for 6-(1,1-dimethylethyl)-α,α,β,β-tetramethyl-1H-pyrazolo[5,1-c]-1,2,4-triazole-3-ethanamine, and hexylamine, the peptoid couplers E1–E8 could be obtained.

Identification of the products by Electrospray mass spectrometry consistently showed formation of the desired materials. Purification and isolation of the resultant couplers was found to be most conveniently achieved by Preparative High Pressure Liquid Chromatography as described below. Using these techniques materials of high purity could be routinely obtained.

Preparative High Pressure Liquid Chromatography—Mass Spectrometry of peptoid coupler combinatorial libraries.

The instrumentation employed for the purification was a Waters-Micromass Preparative HPLC-MS consisting of the following components: a Waters 4000 Preparative HPLC pump, a Gilson 215 Liquid Handler as Autoinjector with 208 racks containing 50 mL Falcon tubes for injection, a second Gilson 215 Liquid Handler as Fraction Collector, a Waters 515 Pump for make up liquid and diluent into a splitter for analytical sampling, a LC Packings custom 1:1000 Preparative Splitter-Diluter for 20–70 mL per min flow rate, and Upchurch adjustable 5:1 splitter, a Waters 996 Photo Diode Array Detector, and a Micromass ZMD Mass Spectrometer with Z-spray design and electrospray probe. This instrumentation was controlled by Mass Lynx Software for methods and settings, Fraction Lynx Software for fraction collection, and Open Lynx software for reporting data.

Samples of crude peptoid products from solid phase synthesis were dissolved in 2 mL of methylene chloride and injected automatically into the flow stream. The column for preparative HPLC was a Waters 4.0×10 cm Deltabond, 15 um, radial compression column held in a RCM module. Separations were achieved by the following general gradient method, where A=pure H$_2$0, B=buffer (0.1% acetic acid), C=acetonitrile, D=isopropanol with the flow rate of 30 mL/minute for each step. Keeping B constant at 10%, C was ramped from 75% to 100% in the first 10 minutes, then the solvent strenth was increased further by ramping to 50% C and 50% D in the next 10 minutes. This was followed by a recycling step as part of the method to enable immediate injection of the next sample. This or similar gradient methods. The flow rate was 30 mL/minute for each step. Gradient methods were incorporated into a general combinatorial separation method (sample list in Mass Lynx) for the purification of combinatorial samples in sequential order. The gradient method was designed to facilitate maximum separation of components in the reaction mixtures, and included column wash and equilibration steps to allow for rapid recycling to allow for automated injection of multiple samples. By this method a new compound could be purified every 30 minutes.

Mass spectral and UV-vis data was accumulated during each preparative HPLC run, including during the particular time of fractionation for the component of interest. This method ensured isolation of pure products only (generally over 95%) for each sample in rapid sequential order. This data could be reported by either manually selecting data for that period of time during a fraction or peak, or by automatically generated for each peak by Open Lynx software, which generated a report summarizing chromatographic and spectral data.

EXAMPLE 2

Synthesis of Coupler B1

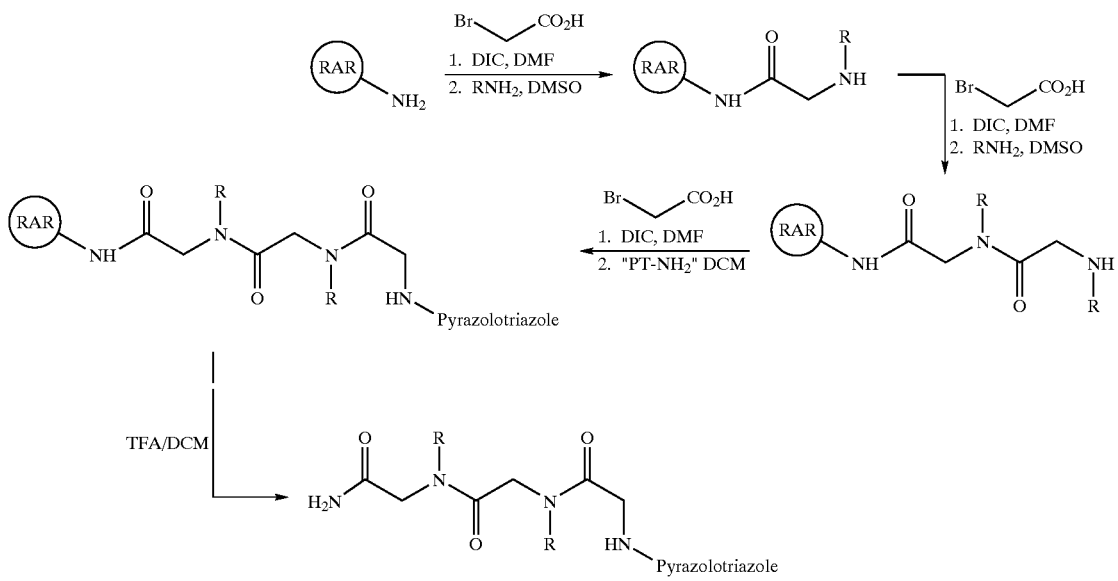

Step 1. Into a 5 mL reaction vessel containing 0.2 grams of Rink-NH2 resin, described above, was added 3 mL of 0.6 Molar solution of bromoacetic acid in dimethylformamide and 1 mL of 3.2 Molar solution of diisopropylcarbodiimide in dimethylformamide. The vessel contents were mixed at room temperature for 30 minutes, drained and the operation repeated twice more. The resin was then washed eight times with 4 mL of dimethylformamide with 3 minutes agitation during each wash. After draining the wash solvent, a 4 mL solution of 2.0 Molar cyclohexylamine in dimethylsulfoxide was added. The resin reaction mixture was agitated for 18 hours at room temperature then drained. The resin was then 15 washed eight times with 4 mL dimethylformamide each for 3 minutes agitation.

Step 2. After draining the wash solvent, was added 3 mL of 0.6 Molar solution of bromoacetic acid in dimethylformamide and 1 mL of 3.2 Molar solution of diisopropylcarbodiimide in dimethylformamide. The vessel contents were mixed at room temperature for 30 minutes, drained and the operation repeated twice more. The resin was then washed eight times each with 4 mL of dimethylformamide with 3 minutes agitation during each wash. After draining the wash solvent, a 4 mL solution of 2.0 Molar cyclohexylamine in dimethylsulfoxide was added. The resin reaction mixture was agitated for 18 hours at room temperature then drained. The resin was then washed eight times with 4 mL dimethylformamide each for 3 minutes agitation.

Step 3. After draining the wash solvent, was added 3 mL of 0.6 Molar solution of bromoacetic acid in dimethylformamide and 1 mL of 3.2 Molar solution of diisopropylcarbodiimide in dimethylformamide. The vessel contents were mixed for 30 minutes, drained and the operation repeated twice more. The resin was then washed eight times each with 4 mL of dimethylformamide with 3 minutes agitation during each wash. After draining the wash solvent, was added 4 mL of a 0.5 Molar dichloromethane, or optionally dimethylsulfoxide, solution of 6-(1,1-dimethylethyl)-$\alpha,\alpha,\beta,\beta$-tetramethyl-1H-pyrazolo[5,1-c]-1,2,4-triazole-3-ethanamine, Chemical Abstracts Registry Number 210405-85-9 whose preparation has been described in Harder, et. al., U.S. Pat. No. 5,925,503 (July 1999). The resin reaction mixture was agitated for 18 hours at room temperature then drained. The resin was then thoroughly washed eight times each with 4 mL of dimethylformamide, then eight times 4 mL of dichloromethane with 3 minutes agitation during each wash.

Step 4. After draining the wash solvent, the product was cleaved from the resin by treatment with 4 mL of 20% trifluoroacetic acid in dichloromethane (volume %), agitation for 30 min, then draining with collection of the cleavage solution containing product. This operation was repeated twice more and the collected cleavage solutions were combined. The resin was then washed twice with 4 mL of dichloromethane and this solvent was also added to the cleavage solution containing product. The cleavage solution was then concentrated to dryness under vacuum without heat to afford 126 milligrams of product B1 with 97% purity as determined by Reverse Phase High Pressure Liquid Chromatography analysis. Electrospray MS: [MH]+=599 m/e.

Using the above procedure with substitution of 2-ethylhexylamine, dodecylamine, 3-ethoxypropylamine, cyclohexanemethylamine, benzylamine, and hexylamine, all available from the Aldrich Chemical Company, Milwaukee, Wis., U.S.A., for cyclohexylamine the peptoid couplers B2–B25 could be obtained. Product weight, product purity and Electrospray mass spectrum [MH]+ ion are shown in Table I for couplers B1–B25.

Using the above procedure with substitution of 6-(1,1-dimethylethyl)-pyrazolo[5,1-c]-1,2,4-triazole-3-ethanamine, whose preparation as the toluenesulfonic acid salt, Chemical Abstract Registry Number 152602-81-8, is described in Kirschke, et. al., Liebigs Ann. Chem. 1994, 10, 1037–42, for 6-(1,1-dimethylethyl)-$\alpha,\alpha,\beta,\beta$-tetramethyl-1H-pyrazolo[5,1-c]-1,2,4-triazole-3-ethanamine, the peptoid couplers B'1–B'25 could be obtained.

It will be understood by one skilled in the art that repetition of Step 2 in the procedure above would result in a five step procedure for the preparation of Inventive Coupler C1. In this manner, substitution of 2-ethylhexylamine, dodecylamine, 3-ethoxypropylamine, cyclohexanemethylamine, benzylamine, and hexylamine, all available from the Aldrich Chemical Company, Milwaukee, Wis., U.S.A., for cyclohexylamine the inventive couplers C2–C25 could also be obtained.

Substitution of N-[2-[6-(1,1-dimethylethyl)-1H-pyrazolo[5,1-c]-1,2,4-triazol-3-yl]-1,1,2-trimethylpropyl]-2-[2-aminophenoxy]-acetamide, which may be prepared by methods described in Romanet, et. al., U.S. Pat. No. 5,972,587 (October 1999), for 6-(1,1-dimethylethyl)-$\alpha,\alpha,\beta,\beta$-tetramethyl-1H-pyrazolo[5,1-c]-1,2,4-triazole-3-ethanamine, in the above procedure Step 3 will result in the preparation of Inventive Coupler D17. Further, in this manner, substitution of 2-ethylhexylamine, dodecylamine, 3-ethoxypropylamine, cyclohexanemethylamine, benzylamine, and hexylamine, all available from the Aldrich Chemical Company, Milwaukee, Wis., U.S.A., for cyclohexylamine the inventive couplers D1–D22 could also be obtained. Product weight, product purity and Electrospray mass spectrum [MH]+ ion are shown in Table I for inventive couplers D1–D8.

TABLE I

| Inventive Coupler | Product weight | Product purity | ES/MS [MH]+ |
|---|---|---|---|
| A1[a] | 117 mg | 84% | 460 |
| A2[a] | 96 mg | 93% | 490 |
| A3[a] | 102 mg | 92% | 546 |
| B1[a] | 126 mg | 97% | 599 |
| B2[a] | 147 mg | 98% | 630 |
| B3[a] | 92 mg | 93% | 686 |
| B4[a] | 116 mg | 97% | 630 |
| B5[a] | 152 mg | 97% | 660 |
| B6[a] | 112 mg | 95% | 716 |
| B7[a] | 114 mg | 95% | 686 |
| B8[a] | 87 mg | 93% | 716 |
| B9[a] | 73 mg | 93% | 772 |
| B10[b] | 24 mg | 95% | 604 |
| B11[b] | 39 mg | 98% | 606 |
| B12[b] | 53 mg | 95% | 616 |
| B13[b] | 51 mg | 91% | 610 |
| B14[b] | 38 mg | 99% | 606 |
| B15[b] | 56 mg | 95% | 608 |
| B16[b] | 52 mg | 98% | 618 |
| B17[b] | 61 mg | 97% | 612 |
| B18[b] | 73 mg | 98% | 616 |
| B19[b] | 74 mg | 97% | 618 |
| B20[b] | 67 mg | 98% | 628 |
| B21[b] | 70 mg | 97% | 622 |
| B22[b] | 63 mg | 98% | 610 |
| B23[b] | 77 mg | 97% | 612 |
| B24[b] | 107 mg | 98% | 622 |
| B25[b] | 53 mg | 98% | 616 |
| D1[b] | 85 mg | 98% | 753 |
| D2[b] | 96 mg | 98% | 755 |

TABLE I-continued

| Inventive Coupler | Product weight | Product purity | ES/MS [MH]+ |
|---|---|---|---|
| D3[b] | 125 mg | 98% | 765 |
| D4[b] | 105 mg | 98% | 759 |
| D5[b] | 100 mg | 98% | 755 |
| D6[b] | 102 mg | 97% | 757 |
| D7[b] | 106 mg | 98% | 767 |
| D8[b] | 93 mg | 97% | 761 |

Note:
[a]Crude product weight and crude product purity reported
Note:
[b]Isolated product weight and isolated product purity reported It will be recognized by one skilled in the arts of imaging science that dyes of the current invention may be used in such technologies as thermal dye transfer and ink jet imaging, but are in no wise limited to those technologies. Dyes of the present invention can be prepared by reactions and methods described below. Typical syntheses are illustrated by the following examples.

Method of Dye Preparation

There are two methods used to prepare the dyes:

1. A small amount of dry coupler is weighed into a tube with the addition of a dry developer. An organic solvent such as acetonitrile or other common reversed-phase chromatographic solvent is added and the solution sonicated until the coupler has dissolved. An aliquot of aqueous base is added to both dissolve the developer and ionize the coupler. An oxidizing agent such as sodium persulphate is added to form the dye in solution. The total volume of around 20 ml is rapidly transferred to a reversed-phase low pressure chromatographic system where the dye is eventually eluted by applying a solvent gradient. The effluent is monitored using a spectrophotometric detector tuned to an appropriate wavelength. The dye peak is collected and the solvent evaporated. Recovery of dye is usually in the 80%+ efficiency with purities generally averaging better than 98%. The recovered dye is analyzed by mass spectrometry for identity and High Performance Liquid Chromatography for purity prior to making an emulsion.

2. The coupler is used to make the emulsion and the emulsion is coated with additional gelatin and small amounts of silver halide dispersion as described in the dispersion and coating sections. The coupler coating is converted to dye proportional to the amount of oxidant (in this method exposed silver halide) using conventional photographic development. This involves adding photographic developer solution for 1–2 minutes. A water rinse is done after removal of the developer. An aliquot of photographic bleach solution is added for 1 minute to remove any silver halide and then removed. Finally, repeated water rinses remove all residual developing chemicals.

Method of Dye Dispersion Preparation

Many pertinent photographic properties such as hue, bandwidth, and light stability are hugely affected by the chemical formulations of the emulsions which are then coated onto various substrates. The purified dye or coupler is formulated into an emulsion using basically the same process.

1. The initial dye or coupler is weighed and dissolved in an organic solvent for easier transfer. An aliquot is added to a 15 mL polypropylene centrifuge tube with the appropriate coupler solvent. Any formulation addenda such as stabilizers are also added at this time. The organic solvent is evaporated leaving the dye or coupler dissolved in a small pellet of coupler solvent. An additional auxiliary coupler solvent may be added with sonication or heating depending on solubility characteristics of the dye or coupler. The final components consisting of water, surfactant, and gelatin are added to make somewhere on the order of 4 ml of solution. This solution is sonicated using a ¼ inch probe with 150 watts of power at 20 KHz for up to 25 minutes. The resulting emulsion has been shown to have median particle sizes on the order of 0.3 microns. This emulsion is filtered using 0.45 um filters. An aliquot is diluted with water and measured spectrophotometrically to verify the quality. The resulting formulation contains a gelatin concentration between 1–3.5%, dye concentrations of 2–3 millimolar or coupler concentrations 6–14 millimolar. These emulsions are chilled and stored prior to coating Method of Dye Dispersion Ink Jet Coating There are three distinct coating techniques which are used for micro-scale evaluations. Each of these techniques has its benefits and drawbacks. All of the techniques use conventional disposable microtiterplates or special holders which conform to titerplate dimensions. This allows us to use commercially available equipment for both measurement and photographic development.

1. The first technique developed uses a special holder called a fadeplate. This holder accepts various web materials for laying down emulsions using ink-jet or similar technology. Typically a gelatin subbed Estar™ material is held in the fadeplate. The material is held down on a chilled vacuum plate when depositing material. Various devices are used to create patterns of dye emulsion dots which are merged by repeatedly dispensing a pattern with a slight offset. Typically dots are formed from drops of 100 pl to 50 nl. The resulting patterned laydown is allowed to dry at room temperature before measurement of photographic parameters.

2. The second technique involves adding 1–3% gelatin with sufficient dye emulsion and hardener to form 40–60 ul of solution. After mixing, the plate is chill set and then allowed to dry overnight. The resulting plate has a uniformly coated mid section adequate for measurement.

3. The third technique uses a mixture of coupler dispersion, gelatin, hardener, and silver dispersion. The silver dispersion is metered in using ink-jet technology and the plate mixed.. After mixing, the plate is chill set and then allowed to dry overnight. The plate is processed as described in the dye preparation section to form a uniform layer of dye for studies. This technique provides a coating of dye in a matrix which is very close to that found in conventional films and papers.

Method of Coated Dye Light Fade Measurement

There are two major ways which are used to measure Light stability.

1. The fadeplates or titerplates are read spectrophotometrically using a commercial instrument. The spectra are stored in a database with specific information as to composition and exposure for each distinct section of the plate. The plates are mounted on white reflective cards, and a UV filter sheet is taped into place to screen the UV wavelengths. These cards are mounted in a large temperature controlled sphere with a 50 Klux light source revolving in the center. The plates are removed periodically and re-measured until the measurements indicate that about 10% of the dye has been lost. The data is then used to calculate light fade stability metrics. This typically takes on the order of 3 weeks but several plates can be faded simultaneously.

2. A more rapid method can be used with fadeplate type coatings. The coated section is cut out using a razor knife and placed in a modified holder resembling a standard cuvette. A specially modified spectrophotometer has been programmed to expose several cells at a time with 200 Klux of light and periodically collect visible spectra. The data can be plotted and photographic parameters measured in a few hours to days.

The absorbance maximum of the coated dyes of this invention and the relative light fade of the coated dyes of this invention are shown in Table I and are compared to the corresponding data for Comparison Dyes CD-1 and CD-2 whose structures are shown below.

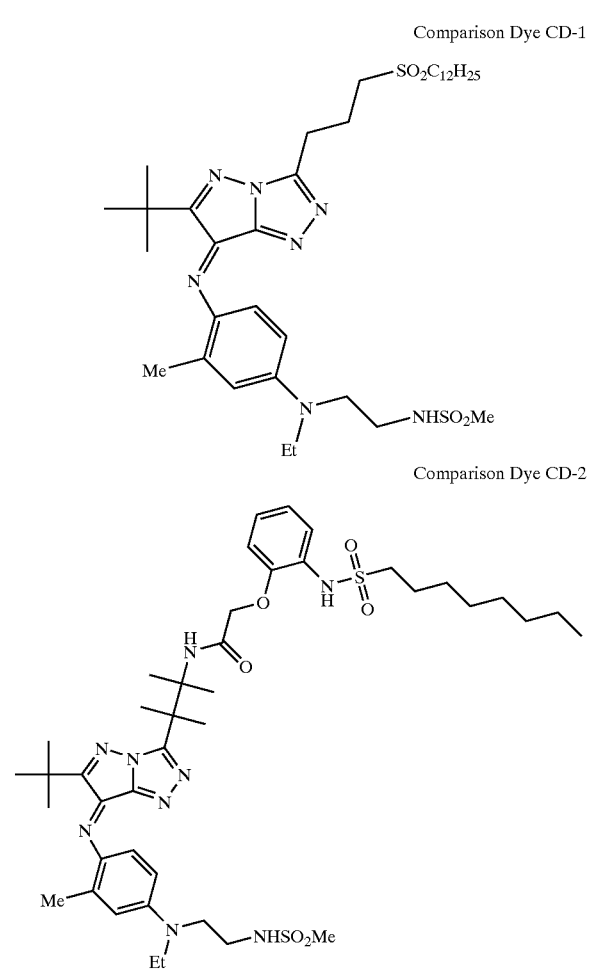

Comparison Dye CD-1

Comparison Dye CD-2

Table II. The invention dyes G1–G12 were formulated as dye dispersions with a stabilizer set. The invention dyes G13 to G28 were formulated as coupler dispersions with stabilizer sets.

| Dye | Absorbance maximum Coated Image | Half Band width Coated Image | Relative light fade |
|---|---|---|---|
| Comparison Dye CD-1 | 545 nm | 90 nm | 2.78 |
| Comparison Dye CD-2 | 549 nm | 74 nm | 1.00 |
| Invention Dye G1 | 550 nm | 84 nm | 4.09 |
| Invention Dye G2 | 550 nm | 76 nm | 2.71 |
| Invention Dye G3 | 550 nm | 77 nm | 2.51 |
| Invention Dye G4 | 550 nm | 79 nm | 2.64 |
| Invention Dye G5 | 550 nm | 78 nm | 1.99 |
| Invention Dye G6 | 550 nm | 80 nm | 2.06 |
| Invention Dye G7 | 550 nm | 79 nm | 3.53 |
| Invention Dye G8 | 550 nm | 78 nm | 1.87 |
| Invention Dye G9 | 550 nm | 78 nm | 2.41 |
| Invention Dye G10 | 550 nm | 79 nm | 2.32 |
| Invention Dye G11 | 550 nm | 77 nm | 2.13 |
| Invention Dye G12 | 550 nm | 78 nm | 1.84 |
| Invention Dye G13 | 555 nm | 84 nm | 1.80 |
| Invention Dye G14 | 556 nm | 77 nm | 1.48 |
| Invention Dye G15 | 554 nm | 78 nm | 1.39 |
| Invention Dye G16 | 554 nm | 78 nm | 1.09 |
| Invention Dye G17 | 555 nm | 76 nm | 1.23 |
| Invention Dye G18 | 556 nm | 76 nm | 1.22 |
| Invention Dye G19 | 555 nm | 76 nm | 1.13 |
| Invention Dye G20 | 554 nm | 75 nm | 2.01 |
| Invention Dye G21 | 556 nm | 77 nm | 1.15 |
| Invention Dye G22 | 556 nm | 76 nm | 0.92 |
| Invention Dye G23 | 555 nm | 76 nm | 1.08 |
| Invention Dye G24 | 555 nm | 76 nm | 0.96 |
| Invention Dye G25 | 554 nm | 76 nm | 0.94 |
| Invention Dye G26 | 556 nm | 74 nm | 0.95 |
| Invention Dye G27 | 556 nm | 76 nm | 1.04 |
| Invention Dye G28 | 555 nm | 76 nm | 0.94 |

The data in Table II indicate that the dyes prepared from the couplers according to the present invention offer good light stability with a deeper absorbance maximum and without unwanted excessive absorbance band shape broadening compared with dye from pyrazolotriazole couplers of the prior art.

The invention has been described in detail with particular reference to certain preferred embodiments thereof, but it will be understood that variations and modifications can be effected within the spirit and scope of the invention.

The entire contents of the patents and other publications referred to in this specification are incorporated herein by reference.

What is claimed is:

1. A process for the preparation of a peptoid substituted azole compound represented by formula I

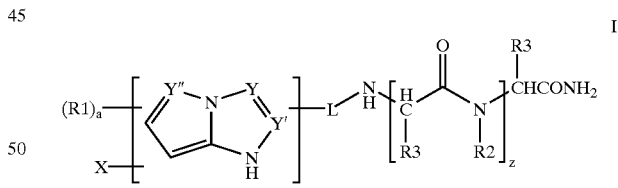

wherein
each R1 represents an independently selected substituent group selected from the group consisting of allyl, vinyl, propargyl, alkyl, aryl, alkoxy, amino, anilino, alkoxycarbonyl, carbamoyl, acyl, cyano, sulfone, and sulfonamide groups, and is 0–1;
each R2 represents an independently selected substituent group selected from the group consisting of alkyl, aryl, and 1-(3-propyl)-2-pyrrolidinone groups;
each R3 represents hydrogen or an independently selected substituent group selected from the group consisting of allyl, vinyl, propargyl, alkyl, aryl, alkoxy, amino, anilino, alkoxycarbonyl, carbamoyl, acyl, cyano, sulfone, and sulfonamide groups;

L represents a single bond or a chain of atoms containing one or more of carbon, nitrogen, oxygen, and sulfur atoms;

Y is carbon, and Y' and Y" are each nitrogen;

X is a hydrogen atom, a halogen atom, a carboxy group, an acyl group, or a group bonded to the coupling position through an oxygen, nitrogen or sulfur atom, and Z is 1–6, comprising
- (I) reacting
  - (i) an amino functionalized pyrazolo[5,1-c]-1,2,4-triazole compound with
  - (ii) a resin bound peptoid oligomer bearing a terminal halogen substituent followed by
- (II) cleavage of the resultant product from the resin surface using a fluorinated organic acid in an inert solvent.

2. The process of claim 1 wherein the resin is a polystyrene resin.

3. The process of claim 1 wherein the resin is a Rink Amide Resin.

4. The process of claim 1 wherein the amino group is a primary amine group.

5. The process of claim 1 wherein the amino is an alkyl or an aryl amine group.

6. The process of claim 1 wherein the terminal halogen substituent is derived from an alpha haloacetic acid.

7. The process of claim 6 wherein the alpha haloacetic acid is 2-bromoacetic acid or 2-bromopropionic acid.

8. The process of claim 1 wherein terminal halogen substituent is chosen from the group of chlorine, bromine, and iodine.

9. The process of claim 1 wherein the fluoro acid is an alpha trifluoro-substituted acid.

10. The process of claim 9 wherein the fluorinated acid is trifluoroacetic acid.

11. The process of claim 1 wherein the inert solvent is selected from the group consisting of dimethylformamide, dimethylsulfoxide, dichloromethane, and ethyl acetate.

12. The process of claim 1 wherein the peptoid oligomer group comprises repetitive glycine or alanine units.

13. The process of claim 1 wherein "a" of the formula I is at least 1 and each R1 independently represents an alkyl, aryl, alkoxy, amino, anilino, alkoxycarbonyl, carbamoyl, acyl, cyano, sulfone, or sulfonamido group.

* * * * *

UNITED STATES PATENT AND TRADEMARK OFFICE
CERTIFICATE OF CORRECTION

PATENT NO.         : 6,946,562 B2
APPLICATION NO. : 10/021408
DATED                  : September 20, 2005
INVENTOR(S)        : Donald R. Diehl et al.

It is certified that error appears in the above-identified patent and that said Letters Patent is hereby corrected as shown below:

At Col. 42, line 59 insert -- a is 0-4-- in place of "is 0-1".

Col. 42, line 43:
    Claim 1 should read as follows:

1.    A process for the preparation of a peptoid substituted azole compound represented by formula I

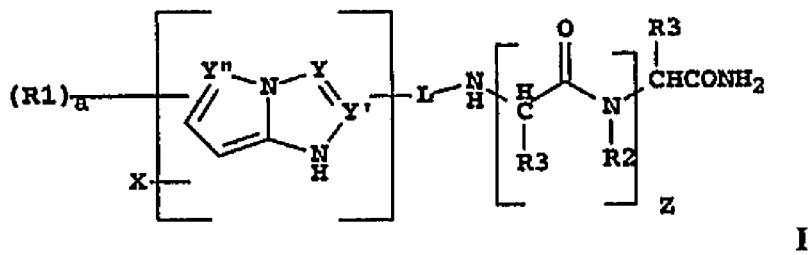

I each R1 represents an independently selected substituent group selected from the group consisting of allyl, vinyl, propargyl, alkyl, aryl, alkoxy, amino, anilino, alkoxycarbonyl, carbamoyl, acyl, cyano, sulfone, and sulfonamido groups and a is 0-4;
    each R2 represents an independently selected substituent group selected from the group consisting of alkyl, aryl, and 1-(3-propyl)-2-pyrrolidinone groups;
    each R3 represents hydrogen or an independently selected substituent group selected from the group consisting of allyl, vinyl, propargyl alkyl, aryl, alkoxy, amino, anilino, alkoxycarbonyl, carbamoyl, acyl, cyano, sulfone, and sulfonamide groups;
    L represents a single bond or a chain of atoms containing one or more of carbon, nitrogen, oxygen, and sulfur atoms;
    Y is carbon, and Y' and Y'' are each nitrogen;
    X is a hydrogen atom, a halogen atom, a carboxy group, an acyl group, or a group bonded to the coupling position through an oxygen, nitrogen, or sulfur atom, and
    Z is 1-6.
comprising
    (I) reacting
        (i) an amino functionalized pyrazolo[5,1-c]-1,2,4-triazole compound with
        (ii) a resin bound peptoid oligomer bearing a terminal halogen substituent followed by

UNITED STATES PATENT AND TRADEMARK OFFICE
CERTIFICATE OF CORRECTION

PATENT NO. : 6,946,562 B2
APPLICATION NO. : 10/021408
DATED : September 20, 2005
INVENTOR(S) : Donald R. Diehl et al.

It is certified that error appears in the above-identified patent and that said Letters Patent is hereby corrected as shown below:

(II) cleavage of the resultant product from the resin surface using a fluorinated organic acid in an inert solvent.

Signed and Sealed this

Thirtieth Day of October, 2007

JON W. DUDAS
*Director of the United States Patent and Trademark Office*